(12) United States Patent
Lewis et al.

(10) Patent No.: US 10,932,489 B2
(45) Date of Patent: Mar. 2, 2021

(54) NICOTINE DELIVERY SYSTEM

(71) Applicant: British American Tobacco (Investments) Limited, London (GB)

(72) Inventors: Scott Lewis, London (GB); Simon James Smith, London (GB); Carl Clement, London (GB); Arlo Blair, London (GB)

(73) Assignee: BRITISH AMERICAN TOBACCO (INVESTMENTS) LIMITED, London (GB)

( * ) Notice: Subject to any disclaimer, the term of this patent is extended or adjusted under 35 U.S.C. 154(b) by 346 days.

(21) Appl. No.: 15/032,364

(22) PCT Filed: Oct. 29, 2014

(86) PCT No.: PCT/EP2014/073263
§ 371 (c)(1),
(2) Date: Apr. 27, 2016

(87) PCT Pub. No.: WO2015/063182
PCT Pub. Date: May 7, 2015

(65) Prior Publication Data
US 2016/0270441 A1    Sep. 22, 2016

(30) Foreign Application Priority Data

Oct. 30, 2013  (GB) .................................... 1319150

(51) Int. Cl.
*A24F 40/48*   (2020.01)
*A61M 11/00*   (2006.01)
(Continued)

(52) U.S. Cl.
CPC .............. *A24F 40/48* (2020.01); *A24F 40/42* (2020.01); *A24F 40/485* (2020.01);
(Continued)

(58) Field of Classification Search
CPC ........ A24F 47/00; A24F 47/008; A24F 40/48; A24F 40/10; A24F 40/40; A24F 40/42;
(Continued)

(56) References Cited

U.S. PATENT DOCUMENTS 1,063,189 A * 6/1913 Dutton .................. B43K 21/08
   401/62
1,485,716 A * 3/1924 Rogers ............... B65D 83/0038
   206/535

(Continued)

FOREIGN PATENT DOCUMENTS

EP     1728529 A1    12/2006
JP     61-177655     11/1986
(Continued)

OTHER PUBLICATIONS

Russian Office Action, Application No. 2016117247, dated Nov. 9, 2017, 6 pages (11 pages with translation).
(Continued)

*Primary Examiner* — Michael J Felton
*Assistant Examiner* — Taryn Trace Willett
(74) *Attorney, Agent, or Firm* — Patterson Thuente Pedersen, P.A.

(57) ABSTRACT

A nicotine delivery system is disclosed. The nicotine delivery system comprises an actuating mechanism and a housing that has a longitudinal axis and defines a chamber that is configured to receive a plunger and has an outlet for the passage of formulation out of the chamber. The actuating mechanism comprises an actuator and an actuation member. The actuator cooperates with the actuation member such that when a plunger is received in the chamber the plunger and the chamber slide relative to each other in an axial direction by a predetermined incremental distance upon each opera-
(Continued)

tion of the actuator to displace a predetermined volume of formulation from the chamber through said outlet.

13 Claims, 33 Drawing Sheets

(51) Int. Cl.
*A61M 16/20* (2006.01)
*A61M 15/06* (2006.01)
*A24F 40/42* (2020.01)
*A24F 40/485* (2020.01)
*A24F 47/00* (2020.01)
*B65D 83/00* (2006.01)

(52) U.S. Cl.
CPC ......... *A24F 47/002* (2013.01); *A61M 11/007* (2014.02); *A61M 15/06* (2013.01); *A61M 16/209* (2014.02); *B65D 83/0033* (2013.01)

(58) Field of Classification Search
CPC ..... A24F 40/485; A61M 15/00; A61M 15/06; B65D 83/0033; B65D 83/0038; B65D 83/0858; B65D 83/0022; B65D 83/0072; B65D 83/0077; B65D 83/0005
See application file for complete search history.

(56) References Cited

U.S. PATENT DOCUMENTS

| | | | | | |
|---|---|---|---|---|---|
| 2,216,476 | A | * | 10/1940 | Mutz | A24F 15/14 221/198 |
| 2,259,133 | A | * | 10/1941 | Harper | B25H 7/04 401/83 |
| 3,263,806 | A | * | 8/1966 | Ring | B65D 81/3834 206/139 |
| 4,090,646 | A | * | 5/1978 | Dubiel | B65D 47/20 222/326 |
| 4,559,955 | A | * | 12/1985 | Brockway | A24F 13/06 131/198.2 |
| 5,044,805 | A | * | 9/1991 | Kosteniuk | B43K 21/06 401/82 |
| 5,560,518 | A | * | 10/1996 | Catterall | B65D 35/28 222/99 |
| 5,617,971 | A | * | 4/1997 | Eason | A61M 15/0045 128/203.21 |
| 5,836,359 | A | * | 11/1998 | Seidler | A61M 5/1782 141/23 |
| 6,415,526 | B1 | * | 7/2002 | Buckner, III | G01B 3/28 33/522 |
| 6,443,151 | B1 | * | 9/2002 | Ruskewicz | A61M 15/00 128/200.24 |
| 9,598,225 | B2 | * | 3/2017 | Patil | B05B 11/0027 |
| 2004/0150690 | A1 | * | 8/2004 | Childers | B05B 15/52 347/22 |
| 2006/0290145 | A1 | * | 12/2006 | Rasmussen | A61M 15/009 292/274 |
| 2008/0029085 | A1 | * | 2/2008 | Lawrence | A61M 15/009 128/200.14 |
| 2008/0177246 | A1 | * | 7/2008 | Sullivan | A61M 11/06 604/520 |
| 2009/0211576 | A1 | * | 8/2009 | Lehtonen | A61M 15/00 128/203.12 |
| 2010/0186739 | A1 | * | 7/2010 | Kronestedt | A61M 5/20 128/203.12 |
| 2010/0300439 | A1 | * | 12/2010 | Djupesland | A61M 15/0028 128/203.15 |
| 2011/0259324 | A1 | * | 10/2011 | Hochrainer | A61M 15/009 128/200.14 |
| 2012/0160873 | A1 | * | 6/2012 | Hsu | B65D 83/0038 222/321.1 |
| 2012/0213576 | A1 | * | 8/2012 | Jaouen | B65D 83/0038 403/321 |
| 2013/0199528 | A1 | * | 8/2013 | Goodman | F22B 1/282 128/203.26 |
| 2015/0136809 | A1 | * | 5/2015 | Hamann | B65D 83/0033 222/260 |
| 2016/0007649 | A1 | * | 1/2016 | Sampson | A24F 7/02 131/187 |

FOREIGN PATENT DOCUMENTS

| | | |
|---|---|---|
| RU | 2336001 C2 | 10/2008 |
| WO | WO 2009069519 | 6/2009 |
| WO | WO 2013128176 | 9/2013 |

OTHER PUBLICATIONS

Japanese Office Action, Application No. 2016-527296, dated Jul. 10, 2017, 3 pages (5 pages with translation).
International Search Report, International Application No. PCT/EP2014/073263, dated Mar. 6, 2015, 3 pages.

* cited by examiner

NICOTINE DELIVERY SYSTEM

PRIORITY CLAIM

The present application is a National Phase entry of PCT Application No. PCT/EP2014/073263, filed Oct. 29, 2014, which claims priority from GB Patent Application No. 1319150.7, filed Oct. 30, 2013, each of which is hereby fully incorporated herein by reference.

TECHNICAL FIELD

The disclosure relates to a nicotine delivery system for administering a substance or formulation.

BACKGROUND

Nicotine delivery systems are known that comprise a mouthpiece, an actuator and a compartment containing a formulation. Upon actuation of the actuator by a user, formulation is released from the compartment and is expelled through the mouthpiece.

SUMMARY

According to embodiments, there is provided a nicotine delivery system comprising a housing that has a longitudinal axis and which defines a chamber that is configured to receive a plunger and has an outlet for the passage of a formulation out of the chamber, and an actuating mechanism comprising an actuator and an actuation member, wherein the actuator cooperates with the actuation member such that when a plunger is received in the chamber the plunger and the chamber slide relative to each other in an axial direction by a predetermined incremental distance in response to each operation of the actuator by a user to displace a predetermined volume of formulation from the chamber through said outlet.

The actuator may be moveable in a direction transverse to the axial direction to cause the plunger and the chamber to slide relative to each other.

In one embodiment, the actuator is mounted to the housing and comprises a button that is depressible inwardly towards the axis to displace the actuation member. In one embodiment, the actuator is slidably received in an aperture in the housing. Alternatively, the actuator may be pivotally mounted to the housing.

In an alternative embodiment, the actuator comprises a diaphragm that is deformable in a direction transverse the axial direction. In one such embodiment, the diaphragm partitions the inside of the housing into first and second compartments and wherein the actuation member is disposed in the first compartment, and wherein one of the first and second compartments comprises a suction channel and the user applies suction to the suction channel to deform the diaphragm in a direction transverse the axial direction. The other of the first and second compartments may be hermetically sealed. Alternatively, the housing may comprise a ventilation aperture that fluidly communicates the other of the first and second compartments with the atmosphere.

The nicotine delivery system may comprise a first biasing means that is configured to bias the actuation member in an axial direction. The nicotine delivery system may comprise a protrusion and a first cam track, wherein in a first position the protrusion is urged against a first stopper surface of a plurality of stopper surfaces of the first cam track to prevent displacement of the actuation member in the direction of the force of the first biasing means. The protrusion may be moveable to a second position in response to actuation of the actuator by the user wherein the protrusion is urged away from the first stopper surface so that the first biasing means displaces the first cam track relative to the protrusion until the protrusion is urged against a second stopper surface of the first cam track.

In one embodiment, one of the actuator and actuation member comprises the protrusion and the other of the actuator and actuation member comprises the first cam track and wherein the actuator is moveable relative to the actuation member to displace the first cam track relative to the protrusion. The first cam track may comprise a plurality of guide channels that are angled with respect to the axial direction and are sequentially arranged in the axial direction to form a zigzag shaped cut-out. One of each of the plurality of stopper surfaces may be disposed at a first end of each of the plurality of guide channels.

In an alternate embodiment, the actuation member comprises one of the protrusion and first cam track and the other of the protrusion and first cam track is held in a fixed position relative to the housing, and wherein the actuator is configured to rotate the actuation member relative to the protrusion to urge the protrusion away from the first stopper surface. The first cam track may comprise a plurality of guide channels that each extends in the axial direction and are arranged in a stepped formation. One of each of the plurality of stopper surfaces may be disposed at a first end of each of the plurality of guide channels.

The actuation member may comprise an actuation surface and wherein the actuator comprises a projection that is configured to be urged against the actuation surface to rotate the actuation member in response to actuation of the actuator by the user. In one such embodiment, the actuation member comprises a second cam track having a plurality of second guide channels that each extends in an axial direction and are arranged in a stepped formation, and wherein each second guide channel comprises a surface facing in a direction transverse the axial direction that comprises an actuation surface. The actuation member may comprise a plurality of ratchet teeth, and wherein each ratchet tooth comprises an actuation surface.

The actuator may be configured such that force exerted on the actuator upon actuation by the user is translated into a force that urges the actuation member in an axial direction.

In one embodiment, one of the actuator and actuation member comprises a protrusion and the other of the actuator and actuation member comprises a cam track that is configured to translate displacement of the actuator in a direction transverse an axial direction into displacement of the actuation member in an axial direction. The cam track may comprise a guide channel that is angled with respect to the axial direction and is configured to receive the protrusion. The guide channel may be formed between first and second guide members, a flexible member and a receiving member of the cam track. The flexible member may comprise a sloping portion that protrudes from a surface of the cam track and has a guide surface at an end thereof that is angled with respect to the axial direction and is configured so that when the actuator is urged towards the actuation member in response to actuation by the user the protrusion is urged against the angled guide surface and is displaced relative to the cam track at an angle to the axial direction. The protrusion may be urged against the sloped portion of the flexible member when the actuator is urged away from the actuation member so that the flexible member flexes to facilitate movement of the protrusion relative to the cam track in a direction transverse the axial direction.

In an alternate embodiment, the actuation member comprises a plurality of ratchet teeth and the actuator comprises an arm and a lever that is pivotally mounted to the arm and is configured so that when the arm is urged in a direction transverse the axial direction in response to actuation by the user an end of the lever arm is urged against one of the ratchet teeth to urge the actuation member in an axial direction. Each ratchet tooth may comprise a connecting surface that extends between adjacent ratchet teeth and an actuation surface that faces in an axial direction, and wherein said end of the lever arm is urged against the actuation surface upon actuation of the actuator by the user. The arm may be integrally formed with the housing. The arm may comprise a resilient material.

In one embodiment, the chamber is integrally formed with the housing. In an alternate embodiment, the chamber comprises a canister that is removably received in the housing. The canister may comprise a plunger. In one embodiment, the actuation member is configured to exert a force on the canister to slide the plunger relative to the chamber upon actuation of the actuator by the user.

The nicotine delivery system may comprise a barrel that defines the chamber for formulation. In one embodiment, the barrel comprises a canister that is received in the housing. In an alternate embodiment, the barrel is integrally formed with the housing.

In one embodiment the actuation member is configured to exert a force on the plunger to slide the plunger relative to the chamber upon actuation of the actuator by the user. In an alternate embodiment, the actuation member is configured to exert a force on the barrel to slide the plunger relative to the barrel upon actuation of the actuator by the user.

In one embodiment, the nicotine delivery system comprises a mouthpiece with an outlet channel that may be fluidly communicated with the chamber of the housing to expel formulation therefrom. The nicotine delivery system may comprise a pressure relief valve that opens to fluidly communicate the housing chamber with the outlet channel when the pressure in the chamber reaches a pressure set-point, the nicotine delivery system being configured so that the pressure set-point is reached when the plunger is slid relative to the chamber upon actuation of the actuator by the user.

In one embodiment, the actuation member is urged away from the mouthpiece in the axial direction upon actuation of the actuator by the user. In such an embodiment, a bore may be disposed in the actuation member that is configured to fluidly communicate the chamber with an outlet of the nicotine delivery system. A seal may be provided between a peripheral wall of the actuation member and the inside of the housing.

In an alternate embodiment, the actuation member is urged towards the mouthpiece in the axial direction upon actuation of the actuator by the user.

The nicotine delivery system may comprise a biasing member that is configured to bias the actuator relative to the housing in a direction transverse the axial direction. A piston may be disposed on an end of the plunger and is slidably received in the chamber.

In one embodiment, the nicotine delivery system comprises the formulation in the chamber. The formulation may contain nicotine. The formulation may comprise tobacco and/or one or more flavors or flavorants. The formulation may be in an aqueous form or may be in a non-aqueous form, such as a powder form or a non-aqueous liquid form.

Embodiments also provide a nicotine delivery system comprising a housing that has a longitudinal axis and which defines a chamber that is configured to receive a plunger and has an outlet for the passage of formulation out of the chamber, an actuation member that is configured such that when a plunger is received in the chamber the actuation member slides the plunger in an axial direction into the chamber to displace formulation from the outlet in response to rotation of the actuation member relative to the housing, a first biasing means configured to rotatably bias the actuation member, and an actuator to hold the actuation member against the bias until actuation of the actuator by a user.

The nicotine delivery system may comprise a screw thread that is configured to translate rotation of the actuation member in a rotational direction into displacement of the actuation member in an axial direction.

In one embodiment, the nicotine delivery system comprises a mating portion that is held in a fixed position relative to the axial direction, and wherein the screw thread is disposed on the actuation member and is configured to cooperate with the mating portion. In an alternate embodiment, the nicotine delivery system comprises a mating portion that is disposed on the actuation member, and wherein the screw thread is held in a fixed position relative to the axial direction and is configured to cooperate with the mating portion. In one embodiment, the mating portion comprises a second screw thread. In an alternate embodiment, the mating portion comprises a protrusion.

The first biasing means may comprise a torsion spring.

The actuator may comprise a first friction component that is configured to engage with a second friction component that is mounted to the actuation member to prevent the actuation member from rotating, the first friction component being urged away from the second friction component upon actuation of the actuator by the user to enable rotation of the actuation member.

The nicotine delivery system may comprise a damper that is configured to damp the motion of the first biasing means.

In one embodiment, the chamber is integrally formed with the housing. In an alternate embodiment, the chamber comprises a canister that is removably received in the housing. The canister may comprise a plunger. In one embodiment, the actuation member is configured to exert a force on the canister to slide the plunger relative to the chamber upon actuation of the actuator by the user.

In one embodiment the actuation member is configured to exert a force on the plunger to slide the plunger relative to the chamber upon actuation of the actuator by the user.

In one embodiment, the nicotine delivery system comprises a mouthpiece with an outlet channel that may be fluidly communicated with the chamber of the housing to expel formulation therefrom. The nicotine delivery system may comprise a pressure relief valve that opens to fluidly communicate the housing chamber with the outlet channel when the pressure in the chamber reaches a pressure set-point, the nicotine delivery system being configured so that the pressure set-point is reached when the plunger is slid relative to the chamber upon actuation of the actuator by the user.

The nicotine delivery system may comprise a biasing member that is configured to bias the actuator relative to the housing in a direction transverse the axial direction.

In one embodiment, the nicotine delivery system comprises the formulation in the chamber. The formulation may contain nicotine. The formulation may comprise tobacco and/or one or more flavors or flavorants. The formulation may be in an aqueous form or may be in a non-aqueous form, such as a powder form or a non-aqueous liquid form.

BRIEF DESCRIPTION OF THE DRAWINGS

Embodiments will now be described, by way of example only, with reference to the accompanying drawings in which.

DETAILED DESCRIPTION

Figure 1:
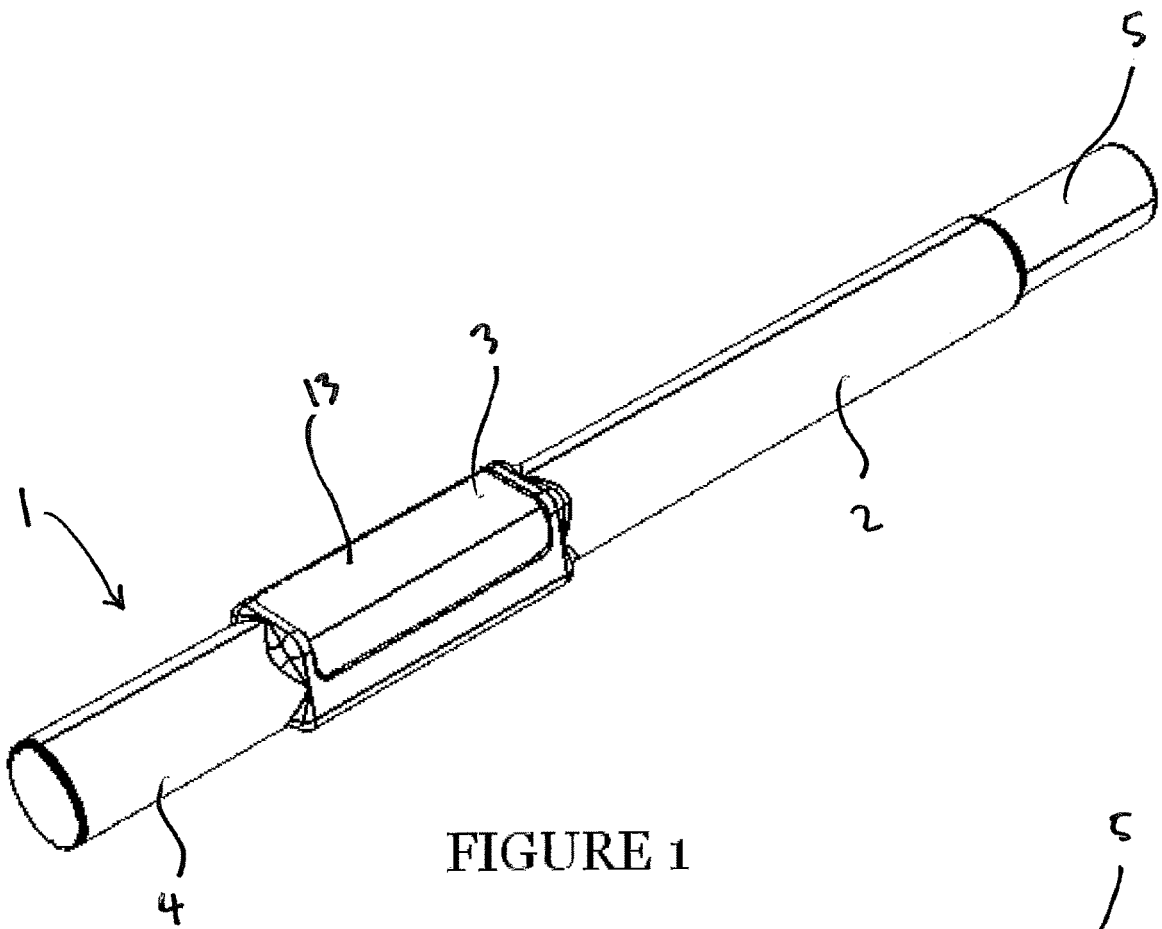
FIG. 1 is a perspective view of a nicotine delivery system according to a first embodiment.
Figure 2:
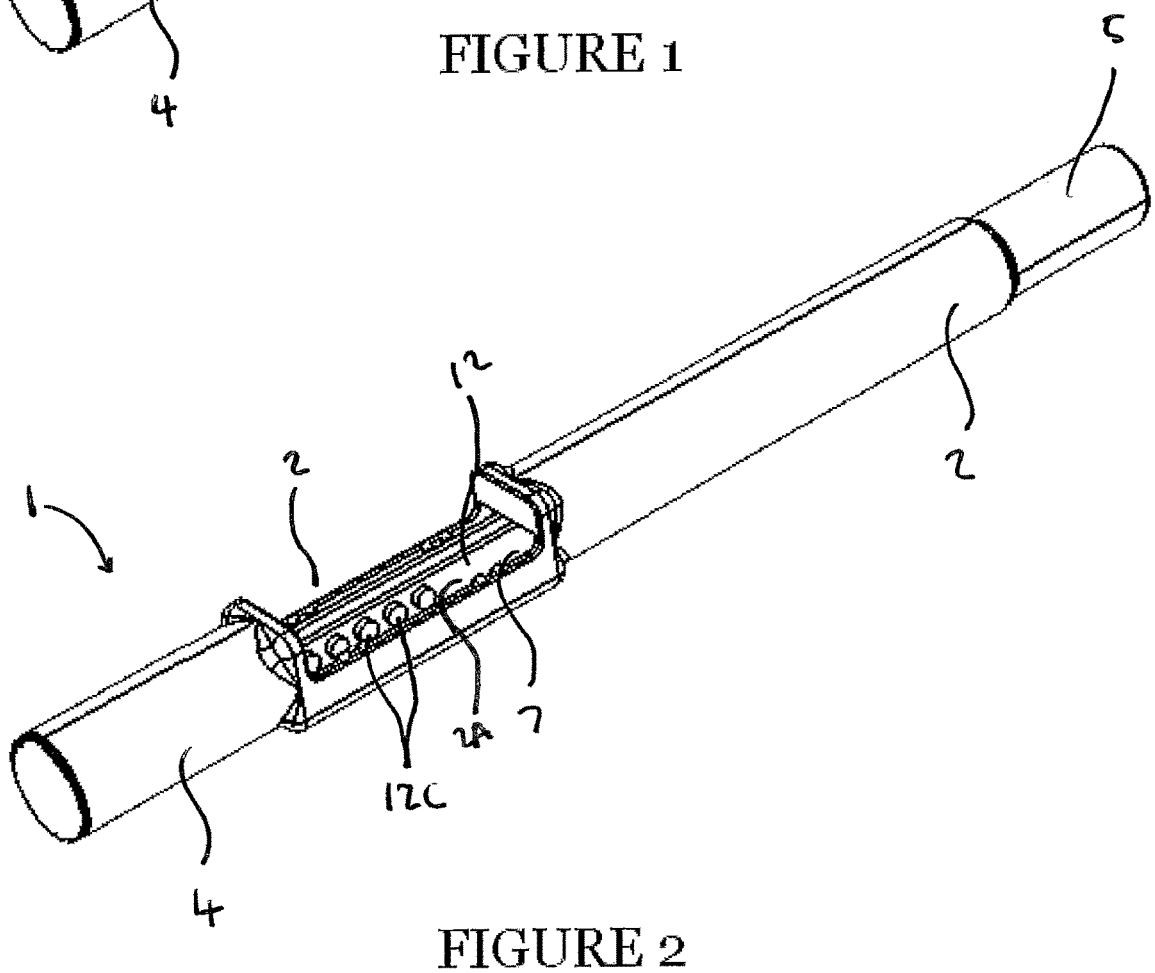
FIG. 2 is a perspective view of part of the nicotine delivery system of FIG. 1.
Figure 3:
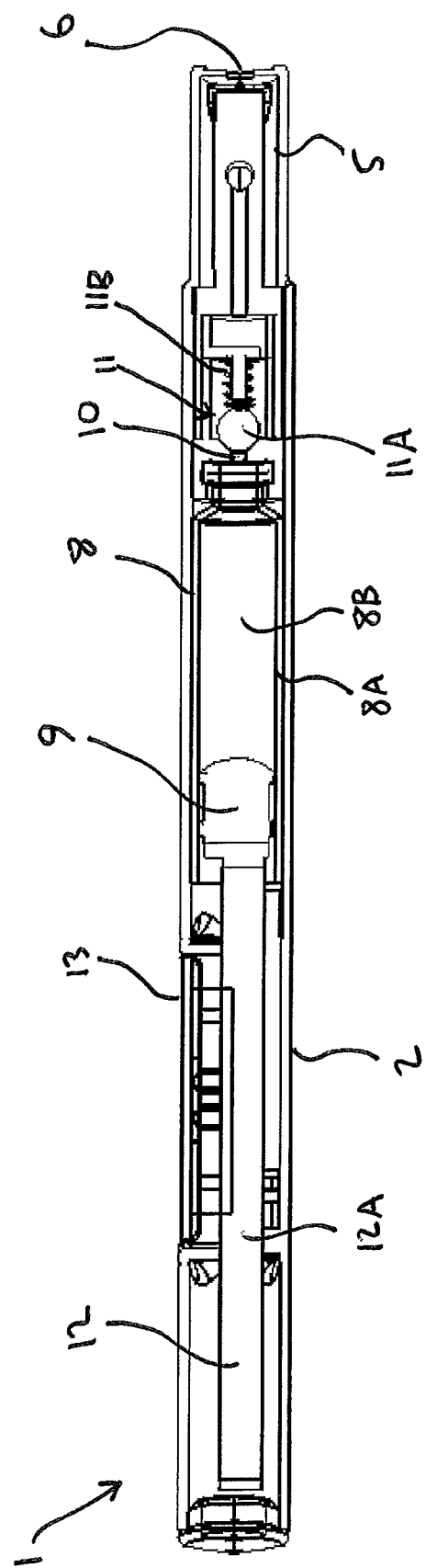
FIG. 3 is a cross-sectional side view of the nicotine delivery system of FIG. 1.
Figure 4:
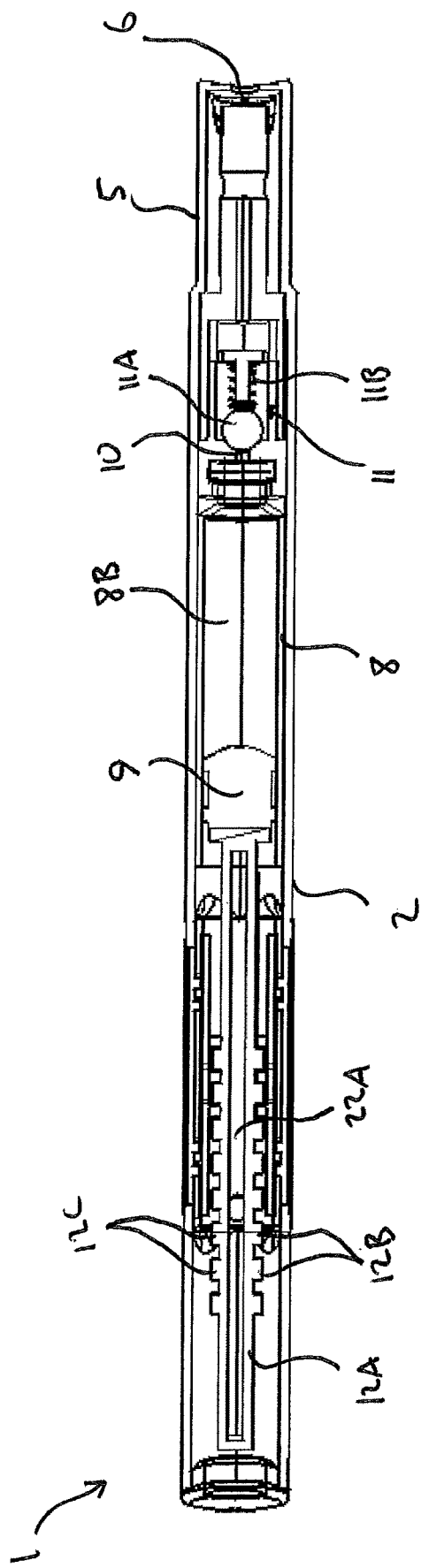
FIG. 4 is a second cross-sectional side view of the nicotine delivery system of FIG. 1.
Figure 5:
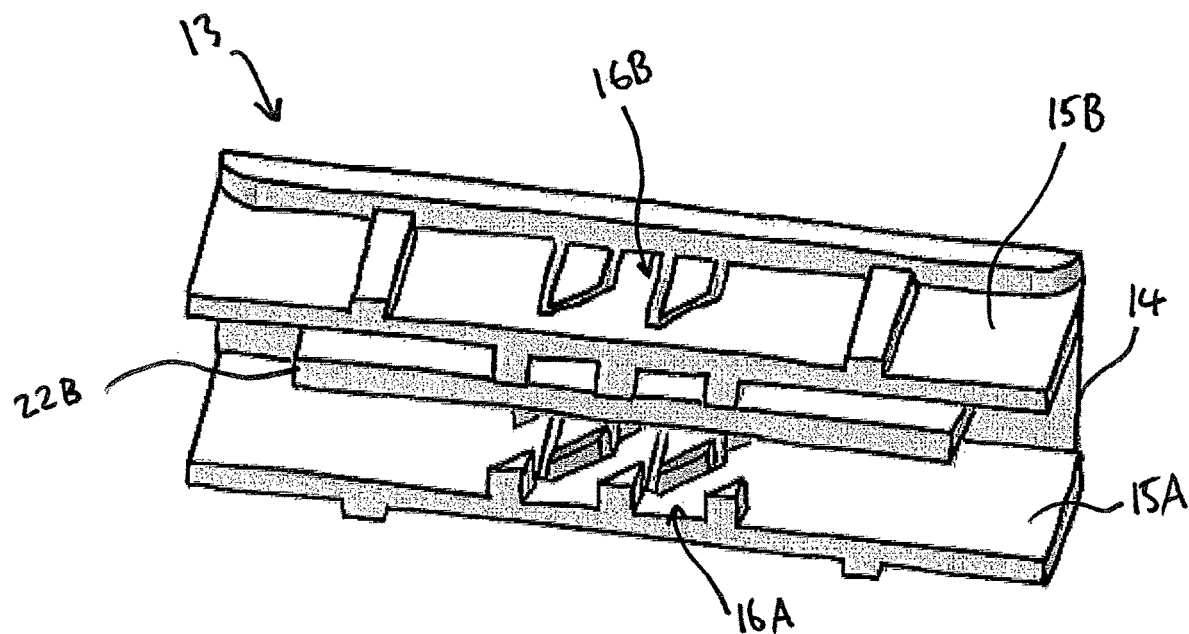
FIG. 5 is a perspective view of an actuator of the nicotine delivery system of FIG. 1.
Figure 6:
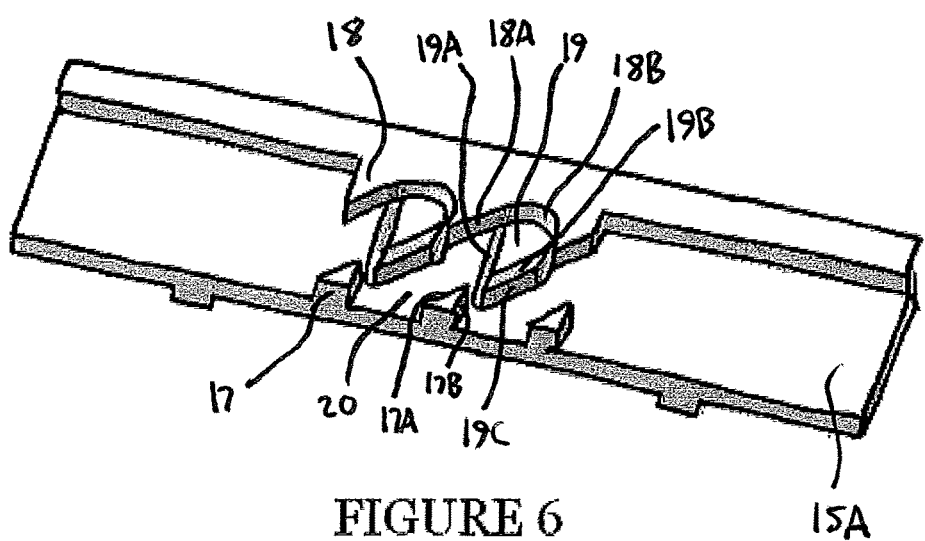
FIG. 6 is a cross-sectional perspective view of the actuator of FIG. 5.

Referring to FIGS. 1-12, a nicotine delivery system 1 according to a first embodiment is shown. The nicotine delivery system may be used as a substitute for cigarette, cigar or like smoking article. The nicotine delivery system 1 comprises an outer housing 2 and an actuating mechanism 3. The outer housing 2 comprises a cylindrical body 4 with a mouthpiece 5 at one end having an outlet channel 6.

An inner space 7 is formed in the cylindrical body 4 and has a chamber 8B that contains a formulation. Although the chamber 8B can be formed directly by the housing itself, the illustrated embodiments show that the chamber 8B is formed from a separate, replaceable, canister 8 disposed in the body 4. The canister 8 comprises a peripheral wall 8A that encloses and defines the chamber 8B. The chamber 8B is sealed at one end by a plunger or piston 9 that is slidably received therein and the opposing end has an outlet 10 that is fluidly communicated with the outlet channel 6.

A pressure relief valve 11 is disposed between the outlet 10 and the outlet channel 6 and is configured to permit the flow of formulation from the chamber 8B to the outlet channel 6 when the pressure of the formulation in the chamber 8B reaches a pressure set-point. The pressure relief valve 11 comprises a valve ball 11A, which is larger in diameter than the barrel outlet 10, and a biasing means 11B. When the pressure in the chamber 8B is below the pressure set-point, the biasing means 11B urges the valve ball 11A into a position in which it seals the outlet 10 to prevent fluid from flowing from the chamber 8B to the outlet channel 6. The pressure relief valve 11 may be urged to an open position, wherein the valve ball 11A is urged away from the outlet 10 so that a gap is formed that allows fluid to flow from the chamber 8B to the outlet channel 6, if the pressure in the chamber 8B is increased so that it exerts a force on the valve ball 11A that is sufficient to overcome the force of the biasing means 11B.

The actuating mechanism 3 comprises an actuation rod or member 12 and an actuator 13. The actuation rod 12 is disposed in the outer housing 2 and is slidable in the longitudinal direction thereof. The actuation rod 12 comprises a longitudinal member 12A with a first and second set of protrusions 12B, 12C arranged sequentially along the length of opposing sides of the longitudinal member 12A.

The actuator 13 comprises a main wall 14 with first and second side walls 15A, 15B co-extending from a major surface of the main wall 14 to form a generally U-shaped member. A button (not shown) is provided on a surface of the main wall 14 that is distal to the side walls 15A, 15B. The first and second side walls 15A, 15B each has an inner surface that faces towards the other of the first and second side walls 15A, 15B. The outer housing 2 comprises an aperture 2A that is configured to slidably receive the actuator 13 so that the actuator 13 may be positioned so that the side walls 15A, 15b extend into the outer housing 2 on opposing sides of the actuation rod 12. The first and second side walls 15A, 15B inner surfaces comprise first and second cam tracks 16A, 16B respectively. The first and second cam tracks 16A, 16B are identical and so only one will be described in detail hereinafter.

The first cam track 16A comprises a plurality of guide members 17, receiving members 18 and flexible members 19. The guide members 17 are arranged longitudinally along the inside surface of the first side wall 15A towards an edge thereof that is distal to the main wall 14. Each guide member 17 comprises a guide surface 17A, that is angled to face towards the main wall 14 and away from the mouthpiece 5 when the actuator 3 is received in the outer housing 2, and a stopper surface 17B that is perpendicular to the main wall 14 and faces towards the mouthpiece 5. The flexible members 19 are each integrally formed with the first side wall 15A and comprise a free end that extends into a corresponding recess 19A in the first side wall 15A in a direction away from the main wall 14. The free end of each flexible member 19 slopes towards the opposing second side wall 15B to form a sloping portion 19B that projects from the surface of the side wall 15A and each free end comprises an angled guide surface 19C that opposes the guide surface 17A of a guide member 17. The receiving members 18 are arranged longitudinally along the first side wall 15A towards an edge thereof that is proximate to the main wall 14. Each receiving member 18 comprises a guide surface 18A that is co-planar to the guide surface 19C of an adjacent flexible member 19 and a curved stopper surface 18B that converges with an end of the guide surface 18A that is proximate to the main wall 14. A guide channel 20 is formed in each space between the guide surface 17A of a guide member 17, the guide surface 19C of a flexible member 19, the sloping portion 19B of an adjacent flexible member 19 and the guide and stopper surfaces 18A, 18B of a receiving member 18.

Figure 7:
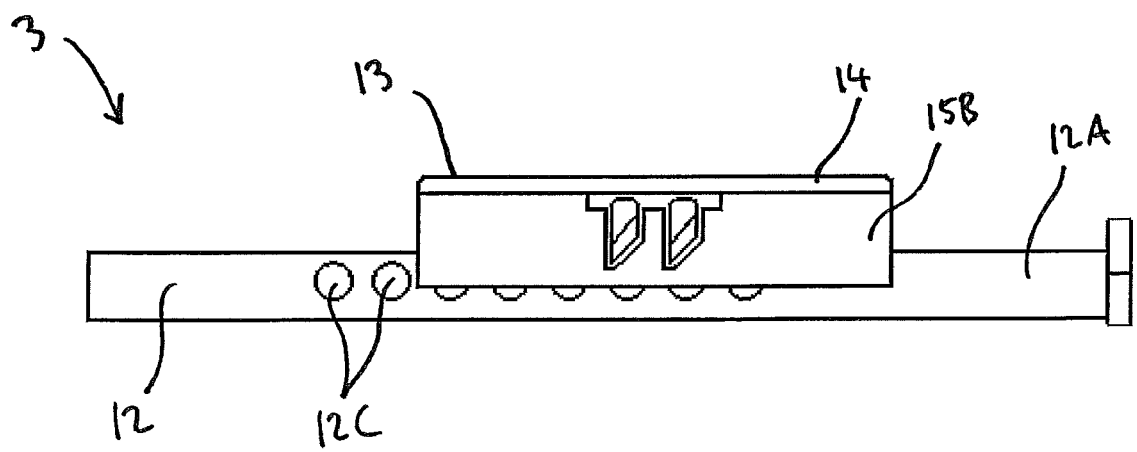
FIG. 7 is a side view of the actuator and an actuation rod of the nicotine delivery system of FIG. 1, in a first position.
Figure 8:
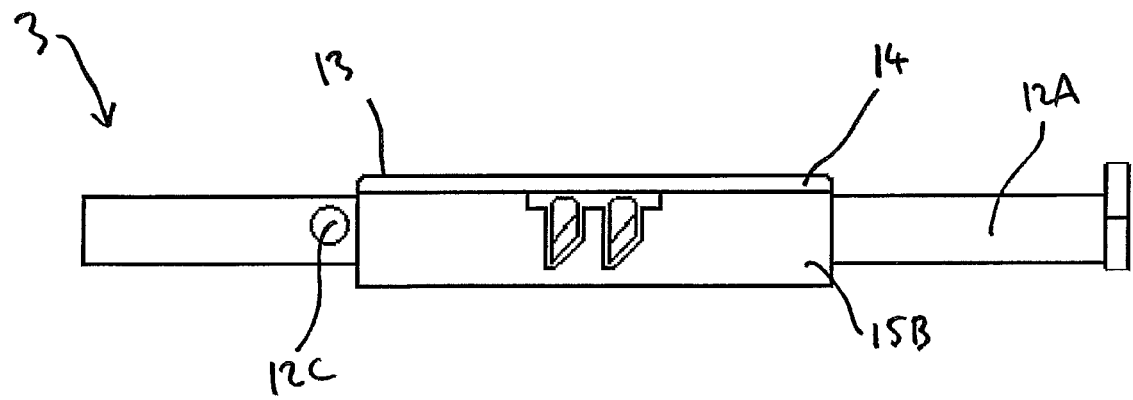
FIG. 8 is a side view of the actuator and actuation rod of FIG. 7, in a second position.
Figure 9:
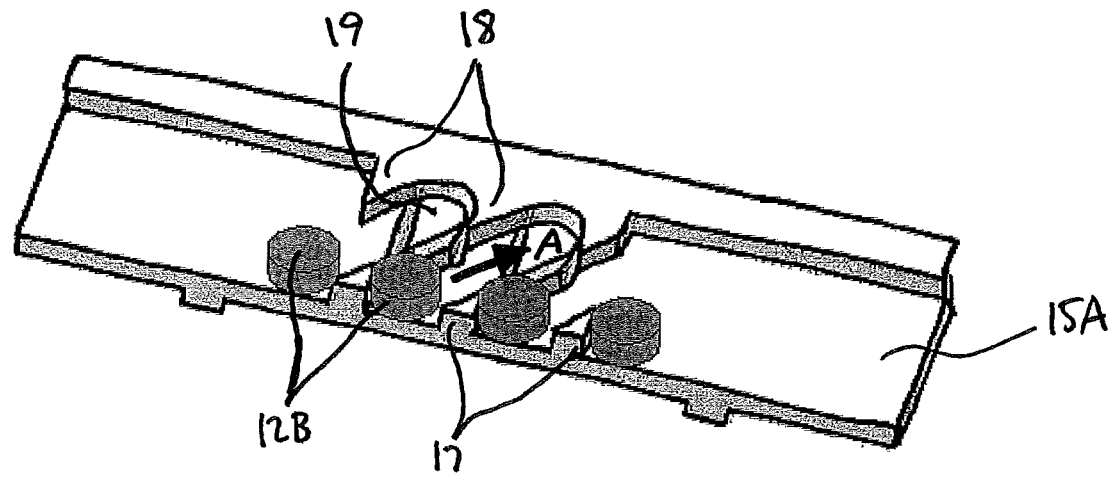
FIG. 9 is a cross-sectional perspective view of the actuator and actuation rod of FIG. 7, in the first position.
Figure 10:
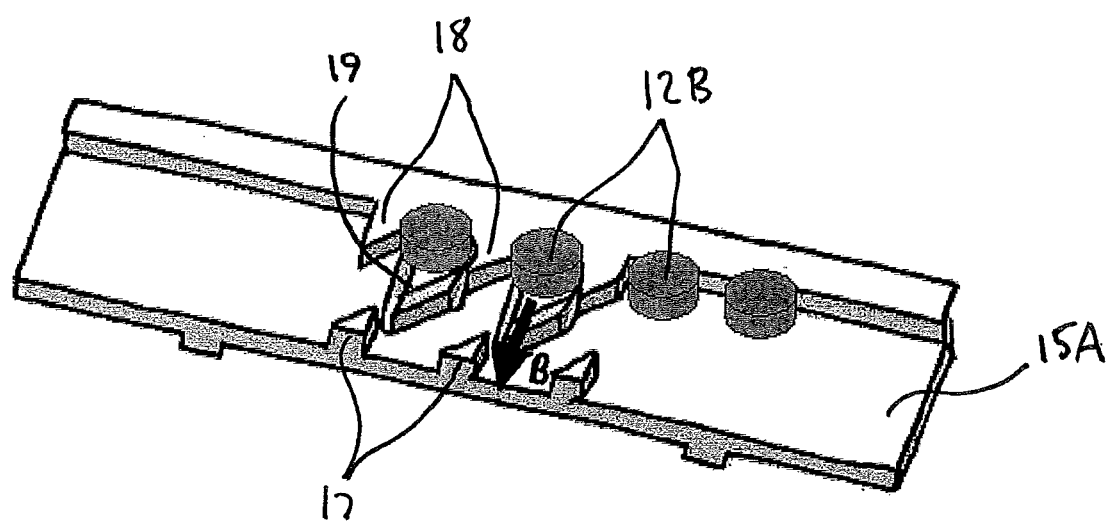
FIG. 10 is a cross-sectional perspective view of the actuator and actuation rod of FIG. 7, in the second position.

The actuator 13 is slidable between a first position, wherein the actuator 13 protrudes out of the aperture 2A in the outer housing 2, and a second position, wherein the actuator 13 is slid further into the aperture 2A in a direction transverse to the longitudinal axis of the cylindrical body 4 or to the direction in which the plunger 9 is movable relative to the chamber 8B. The first set of protrusions 12B engages with the first cam track 16A and the second set of protrusions 12C engages with the second cam track 16B. The first and second cam tracks 16A, 16B are identical and the first and second sets of protrusions are identical 12B, 12C, and so only the engagement between the first cam track 16A and the first set of protrusions 12B will be described in detail. When the actuator 13 is in the first position, a first protrusion 12B of the first set of protrusions 12B abuts the stopper surface 17B of a first guide member 17 (as shown in FIGS. 7 and 9). If a force is applied to the button of the actuator 13 by the user to push the actuator 13 into the second position, the main wall 14 will be urged towards the actuation rod 12. However, the angled guide surface 19C of a first flexible member 19 will prevent the first protrusion 12B from moving directly towards the main wall 14 and so instead the first protrusion 12B will move in a first guide channel 20 (in the direction shown by arrow 'A' in FIG. 9) until the protrusion 12B abuts the curved stopper surface 18B of a first receiving member 18 (as shown in FIGS. 8 and 10). Thus, the first protrusion 12B moves within the first cam track 16A at an angle to the direction that the actuator 13 is urged upon actuation by the user and so the force exerted on the actuator 13 in a direction transverse the longitudinal direction of the outer housing 2 is translated into a force that displaces the actuation rod 12 towards the mouthpiece 5 in the longitudinal direction.

A biasing member (not shown), for example, a spring or portion of resilient material, is disposed between the actuator 13 and the outer housing 2 and biases the actuator 13 in a direction out of the aperture 2A in the outer housing 2. Therefore, when the user releases the button, the first protrusion 12B is each urged away from the stopper surface 18B of the first receiving member 18 and towards the sloping portion 19B of a second flexible member 19 (in the direction shown by arrow 'B' in FIG. 10), which is adjacent the first flexible member 19. The flexible members 19 are manufactured from a material that has some resilience, for example, plastic, rubber or metal, and so the second flexible member 19 will flex within its aperture 19A to sit flush to the inner surface of the side wall 15A, so that the first protrusion 12B can slide over the sloping portion 19B and into a position wherein it lies adjacent to the stopper surface 17B of a second guide member 17, which is adjacent to the first guide member 17. The second flexible member 19 will then return to its original position in which the sloping portion 19B extends out of the inner surface of the side wall 15A. With the actuator 13 returned to its first position, the actuation rod 12 has been slid relative to the actuator 13 so that a second protrusion 12B of the first set of protrusions 12B, which is adjacent to the first protrusion 12B, abuts the stopper surface 17B of the first guide member 17. If the user then presses and releases the button of the actuator 13 again, the second protrusion 12B will move through the first guide channel 20 and then over the second flexible members 19 in the same manner as previously described with respect to the movement of the first protrusion 12B. The remaining protrusions of the first set of protrusions 12B may then be sequentially moved through the first guide channel 20 of the first cam track 16A, in the manner described above, so that the actuation rod 12 is incrementally moveable relative to the actuator 13 upon actuation of the button.

Figure 11:
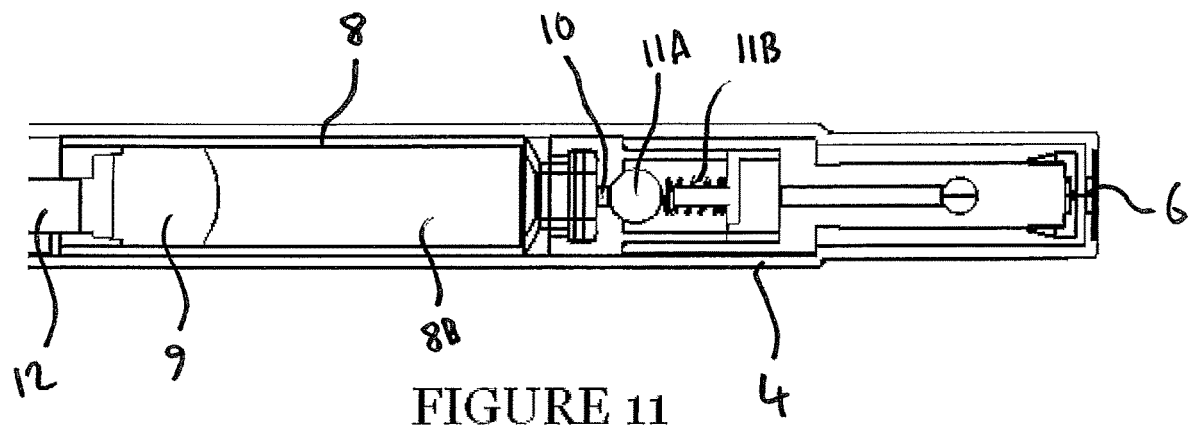
FIG. 11 is a cross-sectional side view of a portion of the nicotine delivery system of FIG. 1, in a retracted position.
Figure 12:
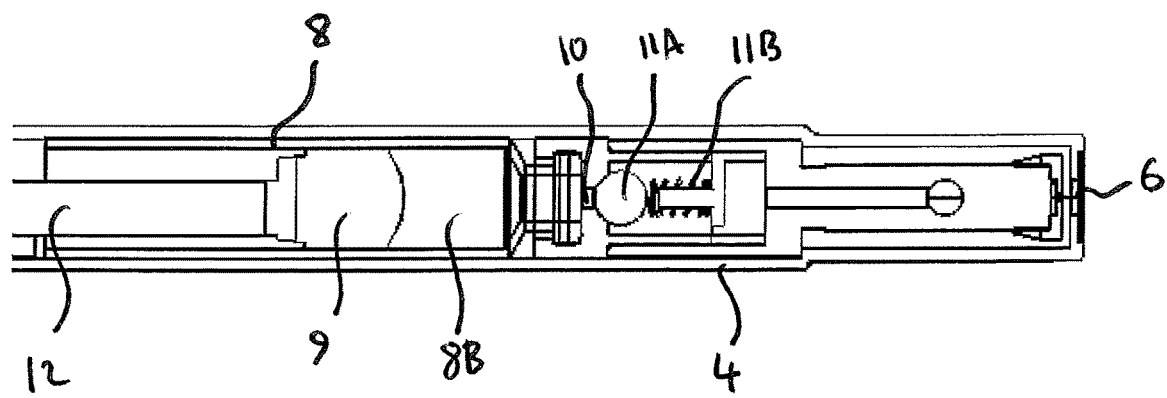
FIG. 12 is a cross-sectional side view of a portion of the nicotine delivery system of FIG. 1, in an extended position.
Figure 13:
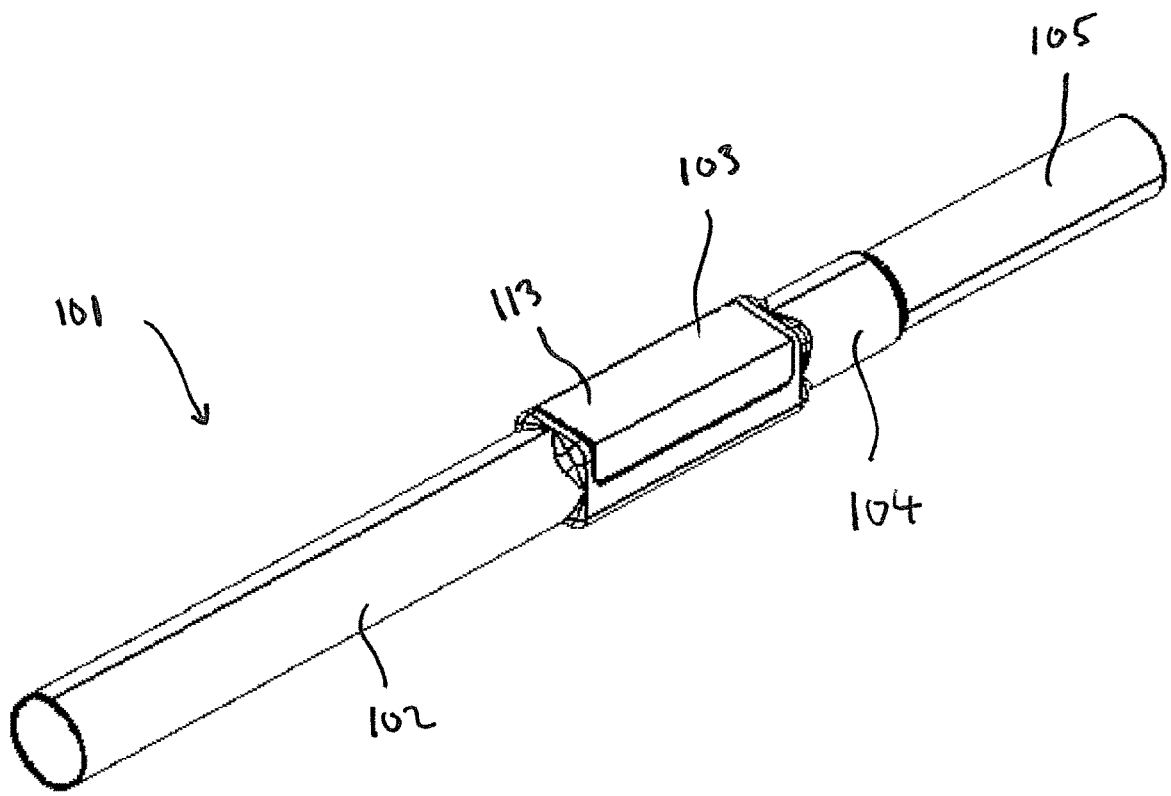
FIG. 13 is a perspective view of a nicotine delivery system according to a second embodiment.
Figure 14:
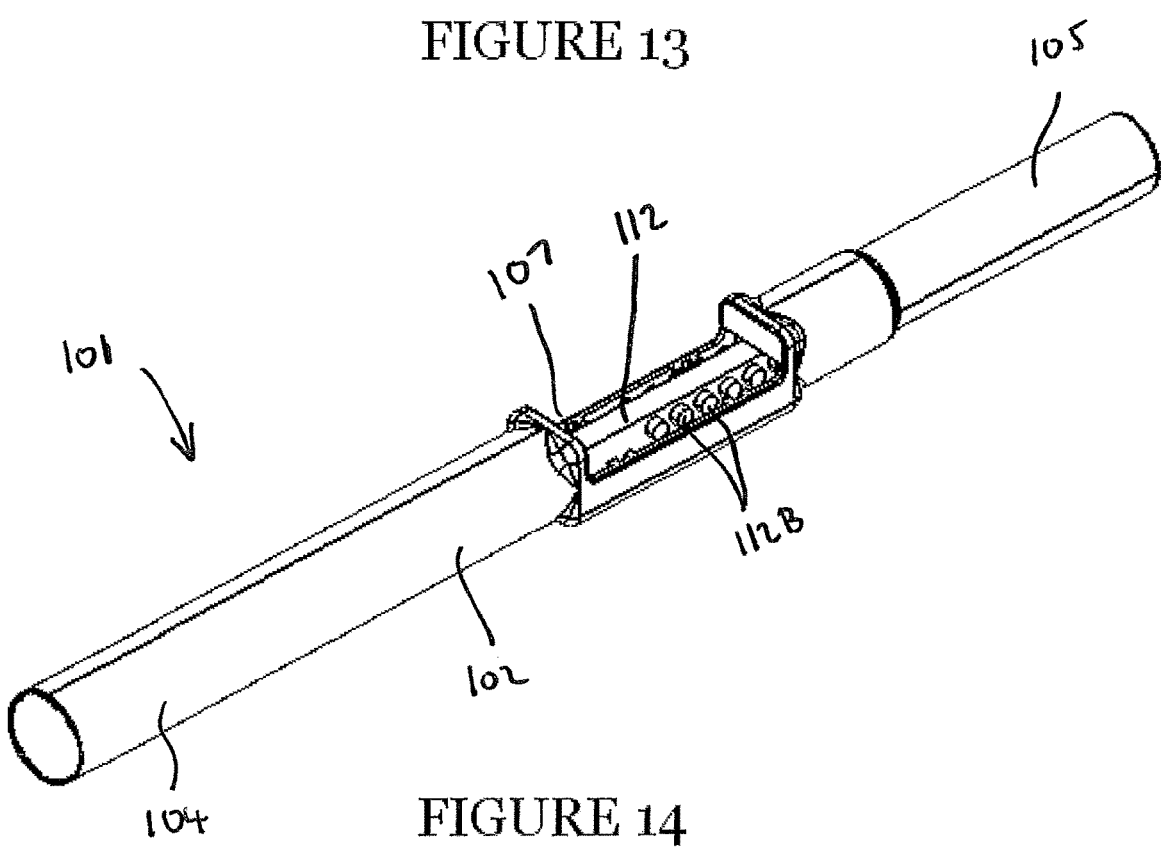
FIG. 14 is a perspective view of part of the nicotine delivery system of FIG. 13.
Figure 15:
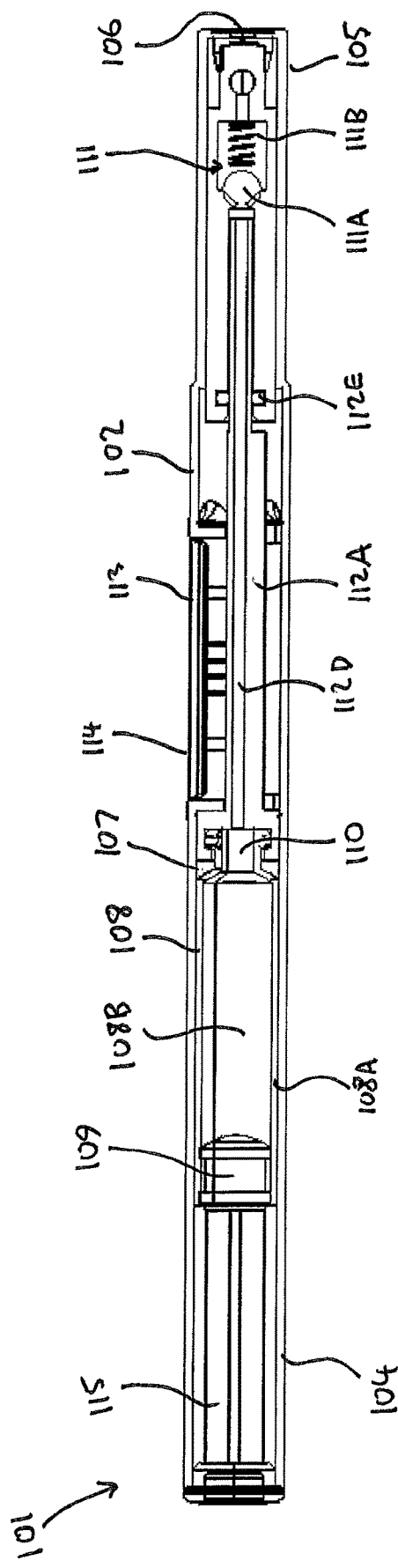
FIG. 15 is a cross-sectional side view of the nicotine delivery system of FIG. 13.
Figure 16:
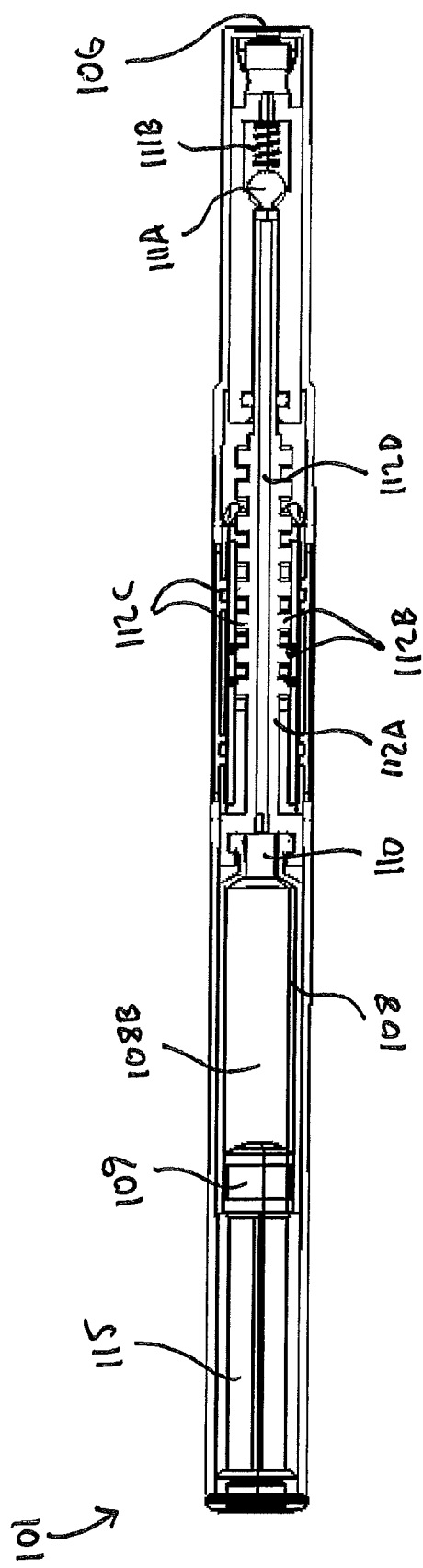
FIG. 16 is a cross-sectional side view of the nicotine delivery system of FIG. 13.

The actuation rod 12 abuts the piston 9 so that when the actuation rod 12 is moved incrementally upon actuation of the actuator 13 the piston 9 is slid within the chamber 8B from a position wherein it is spaced from the outlet 10 (as shown in FIG. 11) to a position wherein it is urged nearer to the outlet 10 (as shown FIG. 12). When the piston 9 moves towards the outlet 10, the volume of the chamber 8B decreases and so the pressure of the formulation in the chamber 8B increases above the pressure set-point required to open the pressure relief valve 11. Therefore, upon actuation of the actuator 13, formulation flows from the outlet 10, through the pressure relief valve 11, and out of the mouthpiece outlet channel 6. As the actuation rod 12 urges the piston 9 relative to the chamber 8B by a predetermined distance upon each actuation of the actuator, a set amount dosage of formulation is released upon each actuation. Therefore, the nicotine delivery system 1 may be configured to release a safe dosage of formulation upon each actuation. The pressure in the chamber 8B then reduces to below the pressure set-point and the pressure relief valve 11 closes. The actuator 13 may then again be actuated by the user to expel further doses of formulation from the mouthpiece 5 until the piston 9 has been slid in the chamber 8B to a position wherein it lies proximate to the outlet 10. When the actuator 13 is in the first position, wherein a force is not exerted on the button by the user, the stopper surface 17B of the first guide member 17 abuts against a protrusion of the first set of protrusions 12B to prevent the actuation rod 12, and thus the piston 9, from being slid in a direction away from the mouthpiece 5 under the force of the pressure of formulation in the chamber 8B.

Although in the above described embodiment the pressure relief valve 11 comprises a valve ball 11A that is urged towards the outlet 10 by a biasing means 11B, in alternate embodiments (not shown) the pressure relief valve 11 may be of a different configuration. For example, the pressure relief valve may comprise a static insert and a sliding insert. In one such embodiment, the sliding insert is slidably received in the outlet channel towards an end thereof that is spaced from the outlet. The sliding insert comprises an outlet aperture therethrough that, in use, vents to the inside of the user's mouth. The static insert comprises an insert passage and a face that is distal to the outlet. The static insert is disposed in the outlet channel between the outlet 10 and the sliding insert and the sliding insert is urged against the face of the static insert by a biasing means so that the aperture is blocked thereby. When the pressure in the chamber 8B reaches the pressure set-point, the pressure is sufficient to overcome the force of the biasing means so that the siding insert is urged away from the face of the static insert so that a gap is formed therebetween, allowing for formulation to flow from the chamber 8B, through the valve outlet and then through the insert passage and out of the outlet aperture, via the gap formed between the static and sliding inserts.

Although in the above described embodiment the pressure relief valve 11 is a separate component to the canister 8 and is positioned between the outlet 10 and the outlet channel 6 of the mouthpiece 5, in an alternate embodiment (not shown) the pressure relief valve 11 is formed integrally with the canister 8 and is disposed in the outlet 10 thereof so that if the canister 8 is removed from the outer housing 2 the pressure relief valve is also removed.

The cylindrical body 4 is formed of two portions that are attachable by a screw thread. Therefore, when the formulation in the chamber 8B has been depleted, it may be replaced by unscrewing the two portions of the cylindrical body 4. In some embodiments, the piston 9 may form part of the canister 8 so that the end of the canister 8 is sealed by a piston 9 when full of formulation so that, when the canister 8 is replaced, the piston 9 is also replaced. In an alternate embodiment (not shown), the end of each canister 8 is sealed by an impermeable material, for example, metal foil or sheet plastic, so that a canister 8 may be stored separately to the nicotine delivery system 1 prior to first use without leakage of the formulation. When a canister has been loaded into the nicotine delivery system, the piston 9 perforates the impermeable material the first time that the actuator 13 is actuated. In such an embodiment, the piston 9 may be provided separately from the canister 8 and thus is not replaced with each canister 8 replacement. In yet another embodiment (not shown), the chamber 8B is integrally formed with the outer housing 2 and so the nicotine delivery system 1 is disposed of, either partially or totally, after depletion of the formulation or, the chamber 8B is refilled.

In the above described embodiment a guide slot 22A is provided in the actuation rod 12 that is configured to slidably receive a guide fin 22B that co-extends with the first and second side walls 15A, 15B of the actuator 13 and is positioned therebetween. Therefore, movement of the actuation rod 12 in a direction transverse the sliding direction of the piston 9 is restricted. In an alternate embodiment, the guide slot 22A and guide fin 22B are omitted.

Although in the above described embodiment the cam tracks are provided with a push button that is urged in a direction transverse the longitudinal direction by the user to move the projections relative to the cam tracks to urge the actuation rod in the axial direction, in an alternate embodiment (not shown) the push button is omitted and instead the cam tracks are provided on a diaphragm, similar in construction to those described in more detail below, and the diaphragm is configured to be urged in a direction transverse the longitudinal direction by the user to move the projections relative to the cam tracks so that the actuation rod is urged in the axial direction and formulation is released.

Although in the above described embodiment the outer housing 2 is generally cylindrical in shape, in alternate embodiments (not shown) the outer housing 2 may be another shape, for example, cuboidal or an elongated cylinder.

Although in the above described embodiment the force acting on the actuation rod 12 to displace it in the longitudinal direction of the outer housing 2 is provided solely by translation of the force exerted on the actuator 13 by the user, in an alternate embodiment (not shown) the nicotine delivery system comprises a second biasing member, for example, a spring or portion of resilient material, that is provided between the actuation rod 12 and an end of the outer housing 2 to bias the actuation rod 12, and thus the piston 9, towards the outlet 10 so that when the actuator 13 is actuated by the user the actuation rod 12 is displaced by the force exerted by the user and the force of the second biasing member. Such an embodiment may reduce the force that must be exerted on the actuator by the user to displace the piston relative to the chamber.

Although in the above described embodiment the actuation rod 12 comprises first and second sets of protrusions 12B, 12C that interface with first and second cam tracks 16A, 16B respectively, in an alternate embodiment (not shown) the second set of protrusions 12C and the second cam track 16B may be omitted.

Referring now to FIGS. 13-18, a nicotine delivery system 101 of a second embodiment is shown. The nicotine delivery system comprises an outer housing 102 and an actuating mechanism 103. The outer housing 102 comprises a cylindrical body 104 with a mouthpiece 105 at one end thereof having an outlet channel 106.

An inner space 107 is formed in the cylindrical body 104 and defines a chamber 108B. The chamber 108B is formed from a canister 108 which is separate to, and removable from, the body 104. The canister 108 comprises a peripheral wall 108A that encloses the chamber 108B containing a formulation. The chamber 108B is sealed towards one end 108 by a piston 109 that is slidably received therein and the opposing end of the chamber 108B comprises an outlet 110.

The actuating mechanism 103 comprises an actuation rod 112 and an actuator 113. The actuation rod 112 is disposed in the outer housing 102 and is slidable in a longitudinal or axial direction. The actuation rod 112 comprises a longitudinal member 112A with a first and second set of protrusions 112B, 112C arranged sequentially along the length of opposing sides of the longitudinal member 112A.

The actuator 113 is similar in construction to the actuator 13 of the first embodiment, and comprises a main wall 114 with first and second side walls (not shown) co-extending from a major surface of the main wall 114 to form a generally U-shaped member. A button (not shown) is provided on a surface of the main wall 114 that is distal to the side walls and the first and second side walls have inner surfaces comprising first and second cam tracks (not shown) respectively. As with the first embodiment, the first and second cam tracks are configured so that a protrusion 112B, 112C of each of the first and second set of protrusions 112B, 112C moves within a respective cam track at an angle to the direction that the actuator 113 is urged upon actuation by the user so that the force exerted on the actuator in a direction transverse the longitudinal direction of the outer housing 102 is translated into a force that displaces the actuation rod 112 in the longitudinal direction. However, unlike the first embodiment, the actuation rod 112 does not urge the piston 109 towards the mouthpiece 105 upon actuation by the user, and instead the piston 109 is disposed towards an end of the nicotine delivery system 101 that is distal to the mouthpiece 105 and is held in a fixed position relative to the outer housing 102 by a second actuation rod 115. Furthermore, the cam tracks of the actuator 113 of the second embodiment are configured so that the actuation rod 112 is urged in a direction away from the mouthpiece 105 when the button is actuated by the user.

The actuation rod 112 is slidably received in the mouthpiece outlet channel 106 and a bore 112D is provided in the actuation rod 112 that fluidly communicates the outlet 110 with the outlet channel 106. A rubber O-ring 112E is provided on the inside of the outlet channel 106 and slidably receives the actuation rod 112. The rubber O-ring 112E provides a seal between the outlet channel 106 and the space between the periphery of the actuation rod 112 and the outer housing 102 to prevent formulation from unintentionally leaking out of the nicotine delivery system 101 when the actuation rod 112 is slid within the housing 102. In an alternate embodiment (not shown) the O-ring 112E is omitted so that formulation is permitted to flow into the space between the periphery of the actuation rod 112 and the outer housing 102 and instead the formulation is prevented from unintentionally leaking to atmosphere by sealing the periphery of the nicotine delivery system 101.

A pressure relief valve 111 is disposed between the bore 112D of the actuation rod 112 and the outlet channel 106 and is configured to permit the flow of formulation from the chamber 108B to the outlet channel 106 when the pressure of the formulation in the chamber 108B reaches a pressure set-point. The pressure relief valve 111 is similar in construction to the pressure relief valve 11 of the first embodiment and comprises a valve ball 111A, which is larger in diameter than the barrel outlet 110, and a biasing means 111B. When the pressure in the chamber 108B is below the pressure set-point, the biasing means 111B urges the valve ball 111A against the outlet 110 to prevent fluid from flowing from the chamber 108B to the outlet channel 106. The pressure relief valve 111 may be urged to an open position, wherein the valve ball 111A is urged away from the outlet 110 so that a gap is formed therebetween that allows for fluid flow from the chamber 108B to the outlet channel 106, if the pressure in the chamber 108B is increased so that it exerts a force on the valve ball 111A that is sufficient to overcome the force of the biasing means 111B.

Figure 17:
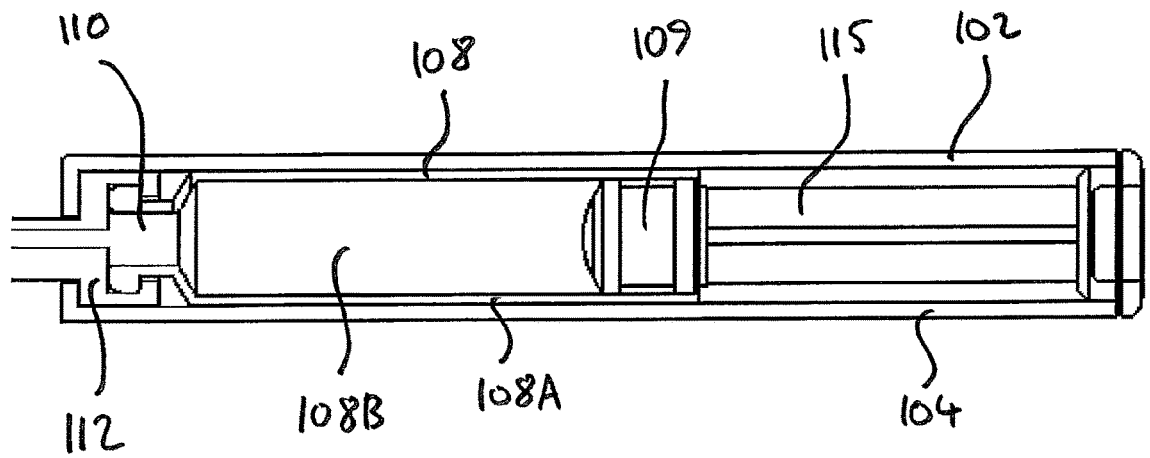
FIG. 17 is a cross-sectional side view of a portion of the nicotine delivery system of FIG. 13, in a first position.
Figure 18:
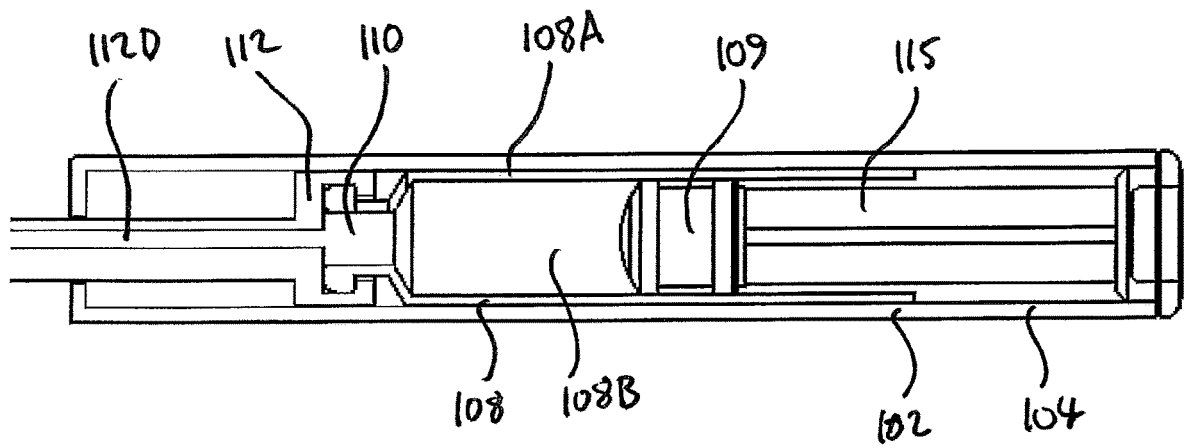
FIG. 18 is a cross-sectional side view of a portion of the nicotine delivery system of FIG. 13, in a second position.
Figure 19:
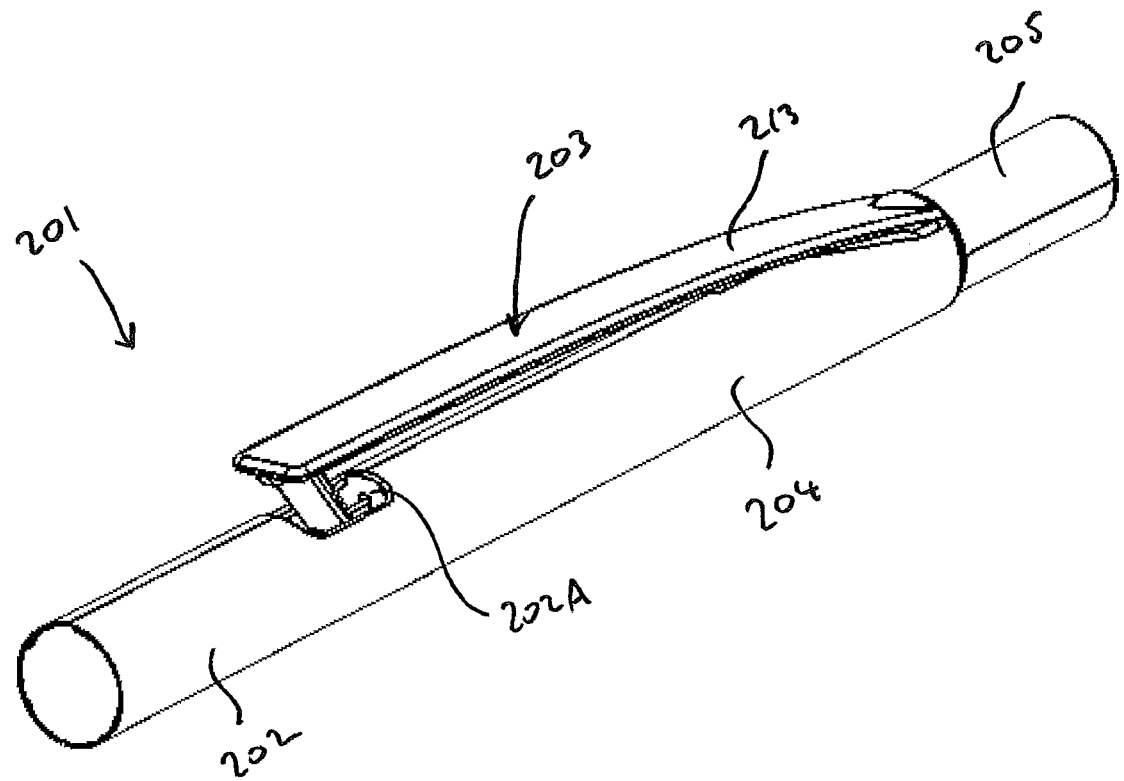
FIG. 19 is a perspective view of a nicotine delivery system of a third embodiment.
Figure 20:
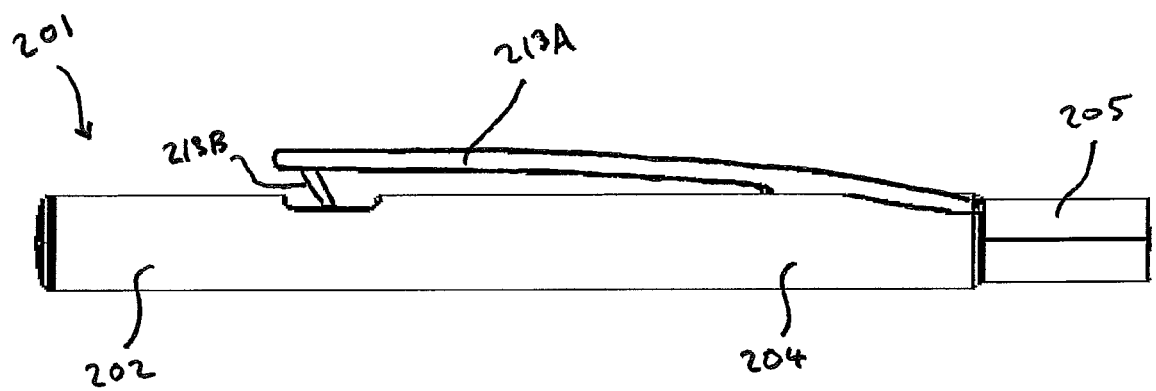
FIG. 20 is a side view of the nicotine delivery system of FIG. 19.

The actuation rod 112 abuts the canister 108 so that when the actuation rod 112 is moved incrementally upon actuation of the actuator 113 the canister 108 is slid within the outer housing 102 from a position wherein the outlet 110 is spaced from the piston 109 (as shown in FIG. 17) to a position wherein the outlet 110 is urged nearer to the piston 109 (as shown in FIG. 18). When the outlet 110 moves towards the piston 109, the volume of the chamber 108B decreases and so the pressure of the formulation in the chamber 108B increases above the pressure set-point required to open the pressure relief valve 111. Therefore, upon actuation of the actuator 113, formulation flows from the outlet 110, through the pressure relief valve 111, via the bore 112D in the actuation rod 112, and then out of the mouthpiece outlet channel 106. The pressure in the chamber 108B then reduces to below the pressure set-point and the pressure relief valve 111 closes. The actuator 113 may then again be actuated by the user to expel further doses of formulation from the mouthpiece 105 until the chamber 108B has been slid relative to the piston 109 to a position wherein the outlet 110 lies proximate to the piston 109. As the actuation rod 112 urges the piston 109 relative to the chamber 108B by a predetermined distance upon each actuation of the actuator 113, a set or predetermined dosage of formulation is released upon each actuation.

Although in the above described embodiment the cam tracks are provided with a push button that is urged in a direction transverse the longitudinal direction by the user to move the projections relative to the cam tracks to urge the actuation rod in the axial direction, in an alternate embodiment (not shown) the push button is omitted and instead the cam tracks are provided on a diaphragm, similar in construction to those described in more detail below, and the diaphragm is configured to be urged in a direction transverse the longitudinal direction by the user to move the projections relative to the cam tracks so that the actuation rod is urged in the axial direction and formulation is released.

Referring now to FIGS. 19-22, a nicotine delivery system 201 of a third embodiment is shown. The nicotine delivery system comprises an outer housing 202 and an actuating mechanism 203. The outer housing 202 comprises a cylindrical body 204 with a mouthpiece 205 at one end thereof having an outlet channel 206 therein.

An inner space 207 is formed in the cylindrical body 204 and has a chamber 208B disposed therein containing a formulation. The chamber 208B may be formed from a separate, removable, canister 208 having a peripheral wall 208A. The chamber 208B is sealed at one end by a piston 209 that is slidably received in the chamber 208B and the opposing end of the chamber 208B comprises an outlet 210.

The actuating mechanism 203 comprises an actuation rod 212 and an actuator 213. The actuation rod 212 is disposed in the outer housing 202 and is slidable in a longitudinal direction. The actuation rod 212 comprises a longitudinal member 212A with a set of ratchet teeth 212B arranged longitudinally along a side of the longitudinal member 212A. Each tooth comprises a first surface 212C and a second surface 212D. The first angled surface 212C is at an angle relative to the longitudinal axis of the outer housing 202 and is angled towards the mouthpiece 205 and towards the actuator 213. The second surface 212D is perpendicular to the longitudinal axis of the outer housing 202 and faces away from the mouthpiece 205.

Figure 21:
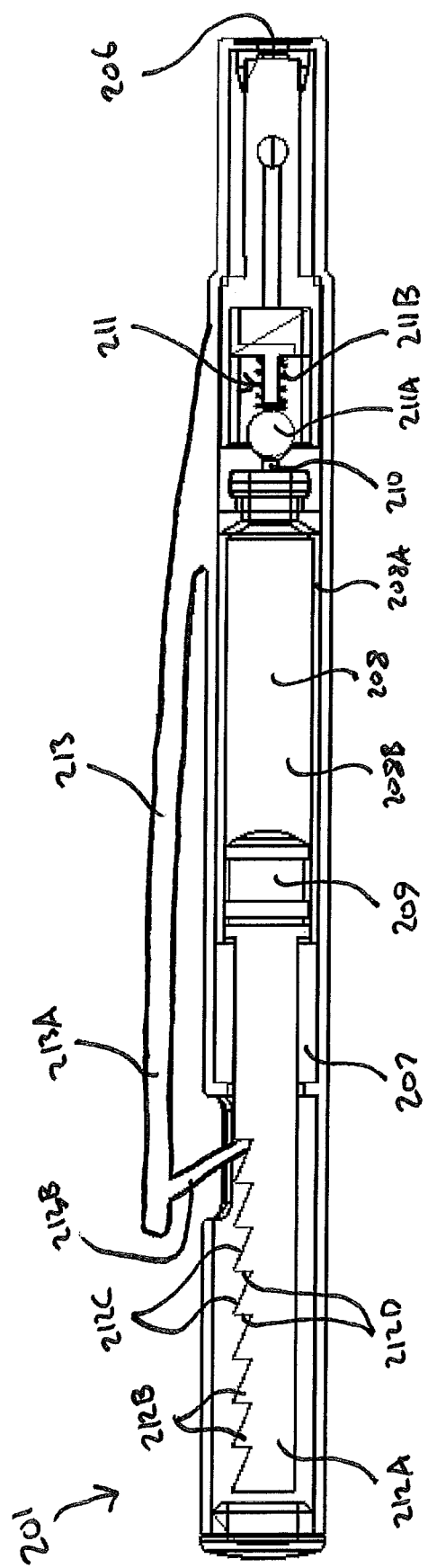
FIG. 21 is a cross-sectional side view of the nicotine delivery system of FIG. 19, in a first position.
Figure 22:
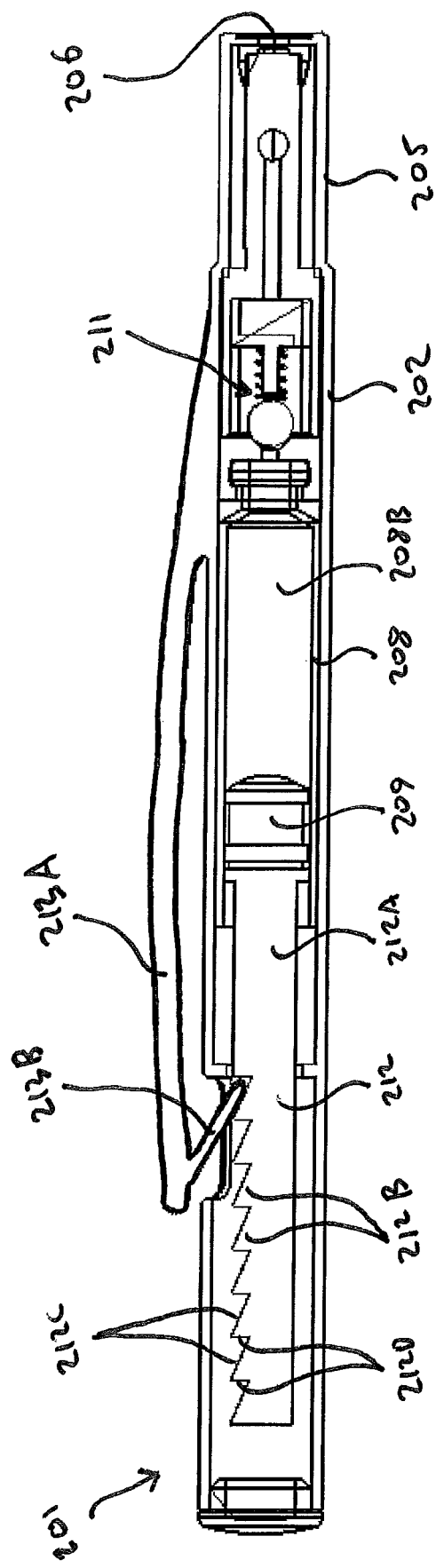
FIG. 22 is a cross-sectional side view of the nicotine delivery system of FIG. 19, in a second position.
Figure 23:
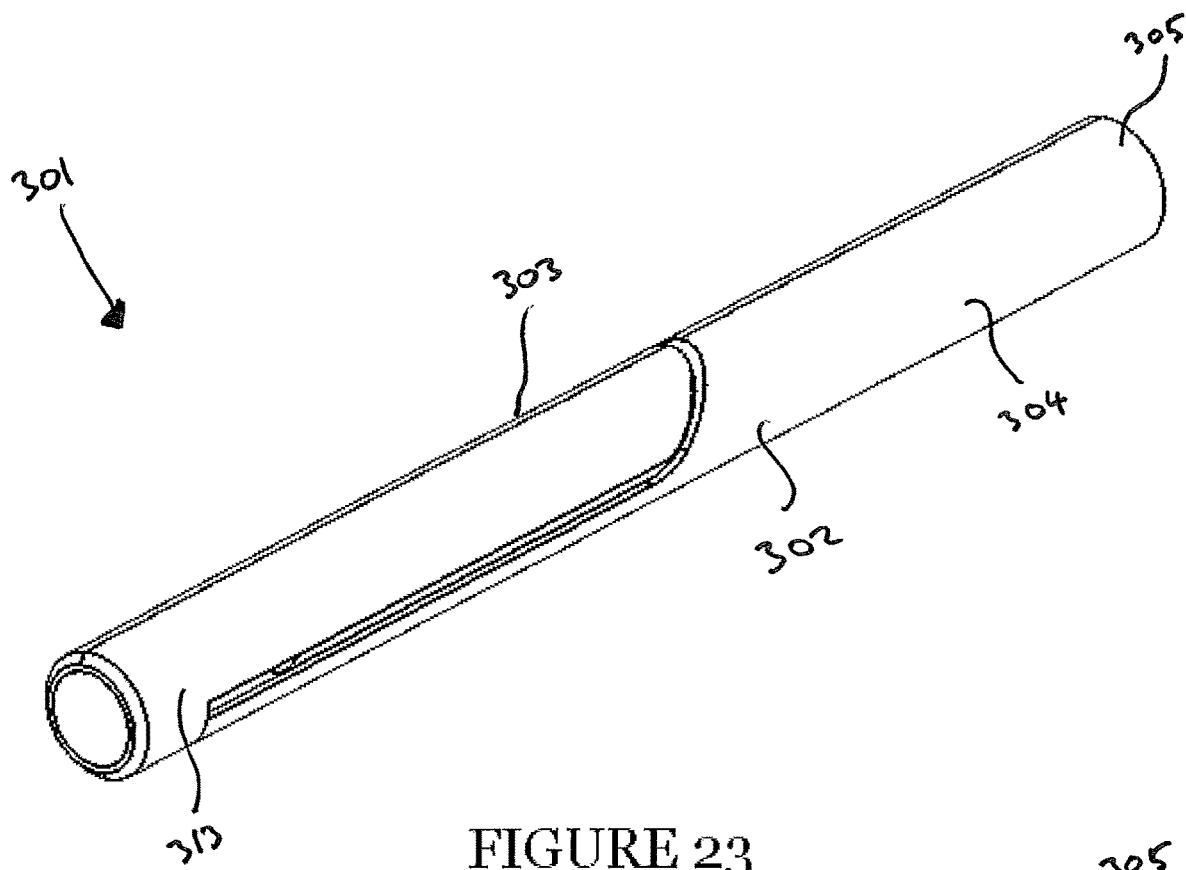
FIG. 23 is a perspective view of a nicotine delivery system of a fourth embodiment.
Figure 24:
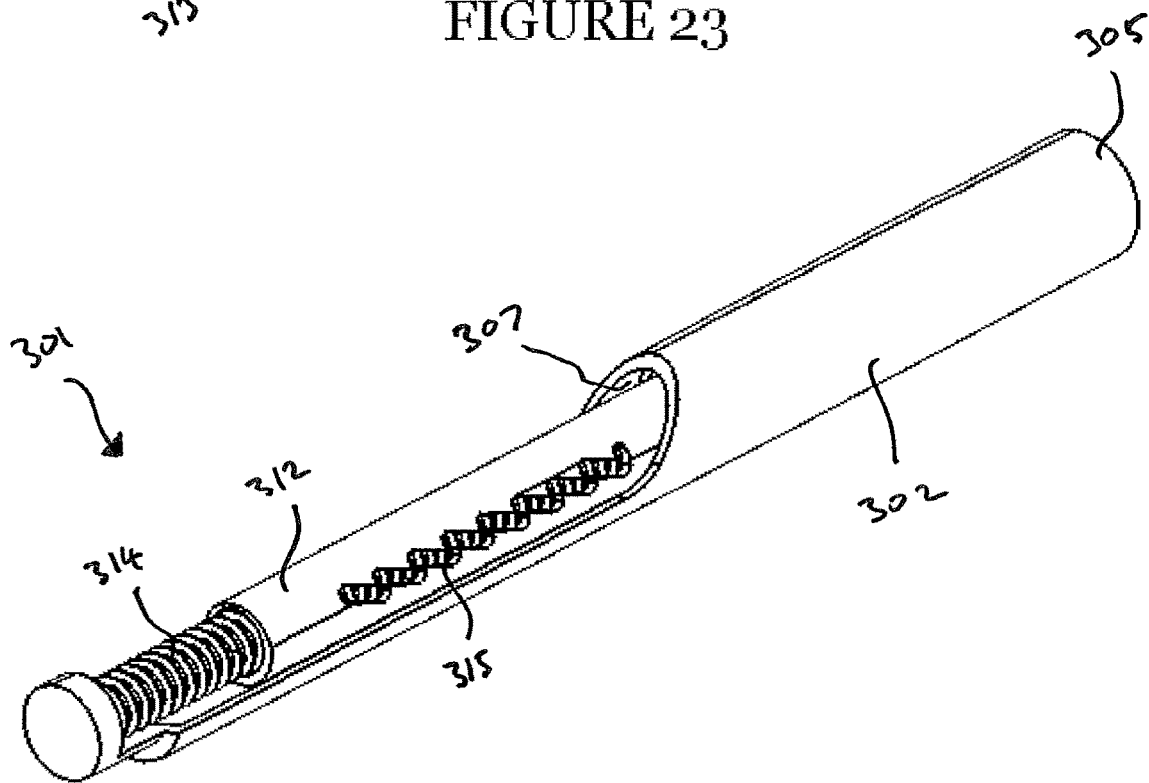
FIG. 24 is a perspective view of part of the nicotine delivery system of FIG. 23.
Figure 25:
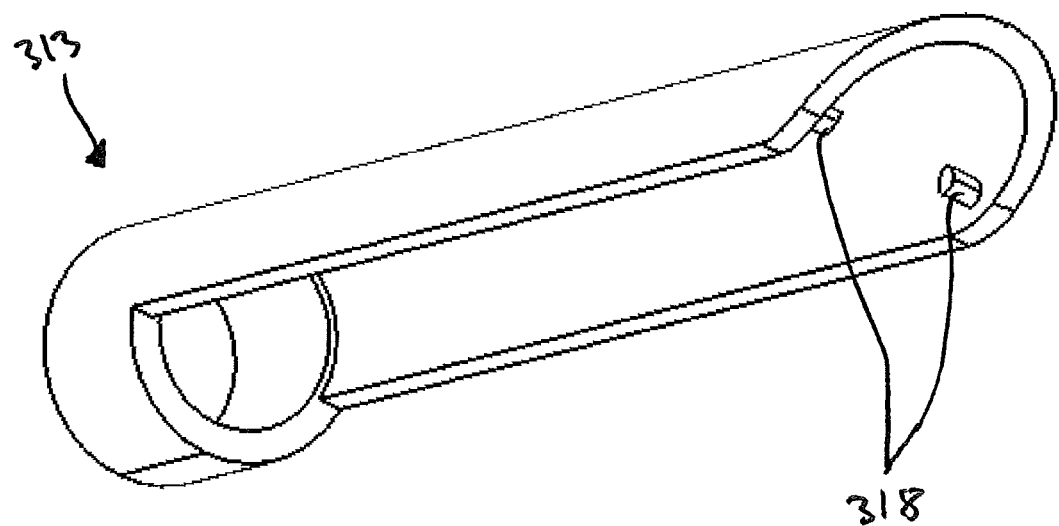
FIG. 25 is a perspective view of an actuator of the nicotine delivery system of FIG. 23.
Figure 26:
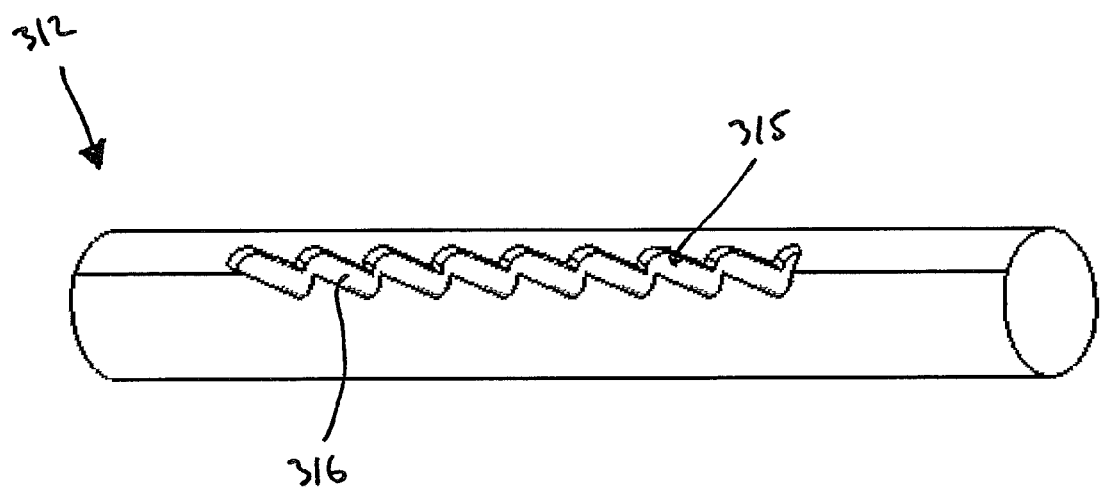
FIG. 26 is a perspective view of an actuation rod of the nicotine delivery system of FIG. 23.
Figure 27:
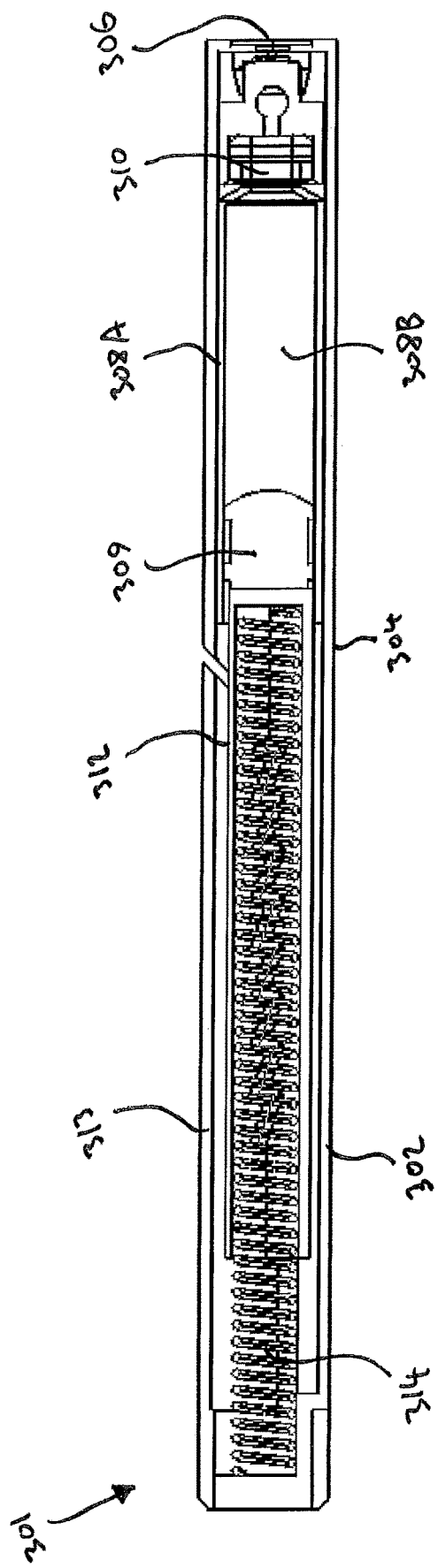
FIG. 27 is a cross-sectional side view of the nicotine delivery system of FIG. 23.

The actuator 213 comprises an arm 213A that extends from the mouthpiece end 205 of the outer housing 2 and has a free end distal to the mouthpiece 205. The arm 213A extends in the longitudinal direction away from the mouthpiece 205 and curves away from the cylindrical body 204 towards the free end so that a gap is formed therebetween when the arm 213A is in a first position (as shown in FIG. 21). The arm 213A is manufactured from a material that has some flexibility and resilience, for example, plastic, rubber or metal, and so the arm 213A may be flexed into a second position by the user wherein the free end of the arm 213A is pressed towards the cylindrical body 204 so that the gap therebetween is decreased (as shown in FIG. 22). A lever 213B extends from the free end of the arm 213 and is pivotal relative thereto. The free end of the lever 213B extends into an aperture 202A provided in the outer housing 202 so that it abuts the second surface 212D of a first tooth 212B of the set of ratchet teeth 212B of the actuation rod 212.

When the arm 213A is in the first position, the lever 213B extends at an angle relative to the arm 213A so that the lever 213B extends towards the longitudinal axis of the outer housing 202 at an angle towards the mouthpiece 205. When the actuator 213 is actuated by the user so that the arm 213A is moved into the second position, the lever 213B pivots relative to the arm 213A and the angle between the lever 213B and the arm 21A decreases so that the lever extends towards the longitudinal axis of the outer housing 202 at an increased angle towards the mouthpiece 205. This pivotal movement of the lever 213B relative to the arm 213A causes the free end of the lever 213B, and thus the second surface 212D of the first tooth 212B it abuts, to be urged towards the mouthpiece 205. Therefore, upon actuation of the actuator 213, the actuation rod 212 is urged towards the mouthpiece 205 in the longitudinal direction of the outer housing 202. When the user no longer exerts a force on the arm 213A, the resilience of the arm 213A causes the arm 213A to be urged back away from the cylindrical body 4 and into its first position.

This causes the lever 213B to pivot relative to the arm 213A so that the angle between the lever 213B and the arm 21A increases and the free end of the lever 213B is urged in the longitudinal direction away from the mouthpiece 205 so that the free end disengages with the second surface of the first tooth 212B and moves over the first surface 212C of an adjacent second tooth 212B until it engages with the second surface 212D of the second tooth 212B. The actuator 213 is then ready to be actuated again by the user to urge the second surface 212D of the second tooth 212 towards the mouthpiece 205. Thus, the actuation rod 212 is incrementally slidable within the housing upon actuation of the actuator arm 213A by the user. When the actuator 213 is in the first position, wherein a force is not exerted on the actuator arm 213A by the user, the lever 213B abuts the second surface 212D of a tooth 212A to prevent the actuation rod 212, and thus the piston 209, from being slid away from the mouthpiece 205.

As with the first embodiment, a pressure relief valve 211 comprising a valve ball 211A and a biasing means 211B is disposed between the outlet 210 and the outlet channel 206 and is configured to permit the flow of formulation from the chamber 208B to the outlet channel 206 when the pressure of the formulation in the chamber 208B reaches a pressure set-point. The actuation rod 212 abuts the piston 209 and so when the actuation rod 212 is moved incrementally upon actuation of the actuator 213 the piston 209 is slid within the chamber 208B towards the outlet 210, causing the pressure of the formulation in the chamber 208B to increase above the pressure set-point required to open the pressure relief valve 211. Therefore, upon actuation of the actuator 213, formulation flows from the outlet 210, through the pressure relief valve 211, and out of the mouthpiece outlet channel 206. The pressure in the chamber 208B then reduces to below the pressure set-point and the pressure relief valve 211 closes. The actuator 213 may then again be actuated by the user to expel further doses of formulation from the mouthpiece 205 until the piston 209 has been slid relative to the chamber 208B to a position wherein it lies proximate to the outlet 210. As the actuation rod 212 urges the piston 209 relative to the chamber 208B by a predetermined distance upon each actuation of the actuator 213, a set or predetermined dosage of formulation is released upon each actuation.

In the above described embodiment the arm 213A is integrally formed with the outer housing 202. In another embodiment (not shown), the arm 213A is attached to the outer housing 202 using an adhesive.

Although in the above described embodiment the actuator arm 213A is manufactured from a resilient material so that it returns to its first position when the arm 213A is released by the user after actuation, in an alternate embodiment (not shown) the comprises a rigid member that is pivotally connected to the cylindrical body and a biasing means, for example, a spring or portion of resilient material, is disposed between the rigid member and the cylindrical body to provide a biasing force to urge the free end of the rigid member arm away from the cylindrical body.

Although in the above described embodiment the actuator 213 comprises an arm 213A that is moved in a direction transverse the longitudinal direction of the outer housing 202 upon actuation to urge the actuation rod 212 in an axial direction, in an alternate embodiment (not shown) the arm 213A is omitted and instead the actuator 213 comprises a diaphragm, similar in construction to those described in more detail below, and the lever 213B is mounted to the diaphragm so that when the user sucks on the mouthpiece 205, the diaphragm is urged towards the actuation rod 212 which causes the lever 213B to rotate so that the free end thereof urges a ratchet tooth 212B towards the mouthpiece 205 to release formulation.

Referring now to FIGS. 23 to 30, a nicotine delivery system 301 of a fourth embodiment is shown. The nicotine delivery system may be a nicotine delivery system and so may be used as a substitute for cigarette, cigar or like smoking article. The nicotine delivery system comprises an outer housing 302 and an actuating mechanism 303. The outer housing 302 comprises a cylindrical body 304 with a mouthpiece 305 at one end thereof having an outlet channel 306 therein.

An inner space 307 is formed in the cylindrical body 304 and has a chamber 308B disposed therein to contain a formulation. The chamber may be defined by the housing itself or it may be a separate, removable, canister 308 having a peripheral wall 308A. The chamber 308B is sealed at one end of by a piston 309 that is slidably received in the chamber 308B and the opposing end comprises an outlet 310.

The actuating mechanism 303 comprises an actuation rod 312, an actuator 313 and a biasing means 314. The actuation rod 312 is disposed in the outer housing 302 and is slidable in the longitudinal direction thereof. The actuator 313 is disposed over a cut-out in the outer housing 302 to enclose the actuation rod 312. The actuation rod 312 comprises a peripheral wall with a space formed therein (not shown) that receives the biasing means 314. First and second cam tracks are formed on opposing sides of the peripheral wall of the actuation rod 312. The first and second cam tracks are identical and so only the first cam track 315 will be described in detail hereinafter.

The first cam track 315 comprises a saw-tooth shaped cut-out 316 formed along the length of the peripheral wall of the actuation rod 312. The cut-out 316 comprises a plurality of guide channels 317 that are cut into the peripheral wall of the actuation rod 312 and are arranged so that they each extend at an angle to the longitudinal axis of the actuation rod 312. Each guide channel 317 comprises a first end 317A that is proximate to the actuator 313 and spaced from the mouthpiece 305 and a second end 317B that is spaced from the actuator 313 and is proximate to the mouthpiece 305. The first end 317A of each guide channel 317 is connected to the second end 317B of an adjacent guide channel 317 to form the saw-tooth arrangement of the cut-out 316. The first end 317A of each guide channel 317 comprises a stopper edge 317C that is perpendicular to the longitudinal axis of the actuation rod 312 and faces towards the mouthpiece 305 when the actuation rod 312 is disposed in the outer housing 302.

Figure 28:
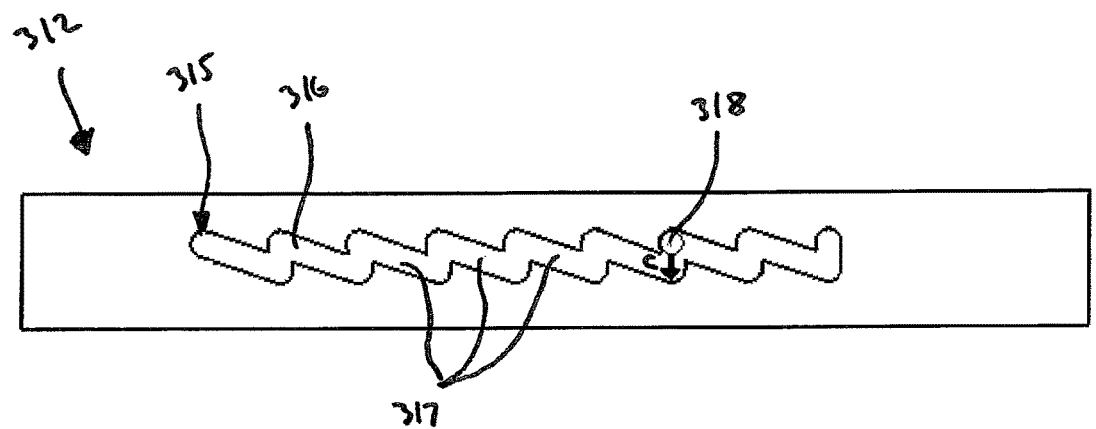
FIG. 28 is a side view of the actuator and actuation rod of FIG. 23, in a first position.

The actuator 313 is pivotally mounted to the outer housing 302 and is rotatable therewith between first and second positions. The actuator 313 comprises a free end and a pair of projections 318 that extend from an inner surface of the actuator 313 and are disposed towards the free end thereof. Each of the projections 318 is configured to be received in a corresponding cam track of the actuation rod 312. The projections 318 are identical and the first and second cam tracks are identical, and so only the engagement between a protrusion 318 and the first cam track will be described in detail. When the actuator 313 is in the first position, the free end of the actuator 313 is spaced from the outer housing 302 and the projection 318 is received in a first end 317A of a first guide channel 317 and locates against the stopper edge 317C (as shown in FIG. 28). The biasing means 314 comprises, for example, a spring or portion of resilient material, and is disposed in the chamber of the actuation rod 312 and is positioned between an end of the actuation rod 312 that is proximate to the mouthpiece 305 and an end of the outer housing 302 that is spaced from the mouthpiece 305 to urge the actuation rod 312 towards the mouthpiece 305 in the longitudinal direction of the actuation rod 312. However, when the actuator 313 is in the first position the actuation rod 312 is prevented from sliding towards the mouthpiece 305 by the projection 318 which is urged against the stopper edge 317C of the first guide channel 317.

Figure 29:
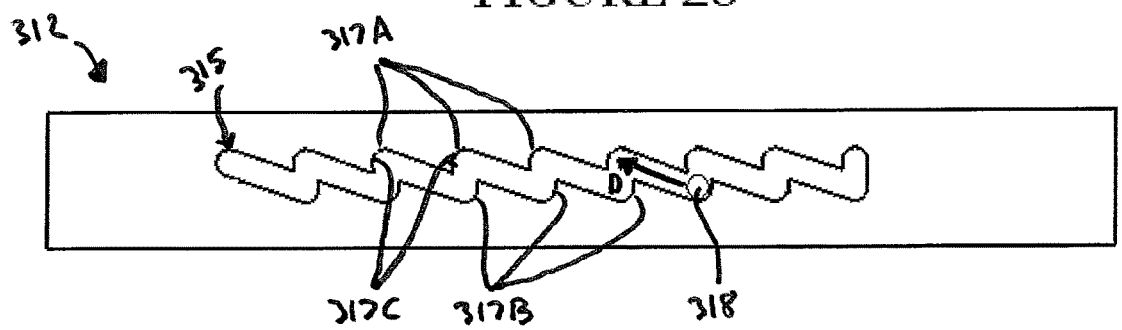
FIG. 29 is a side view of the actuator and actuation rod of FIG. 23, in a second position.
Figure 30:
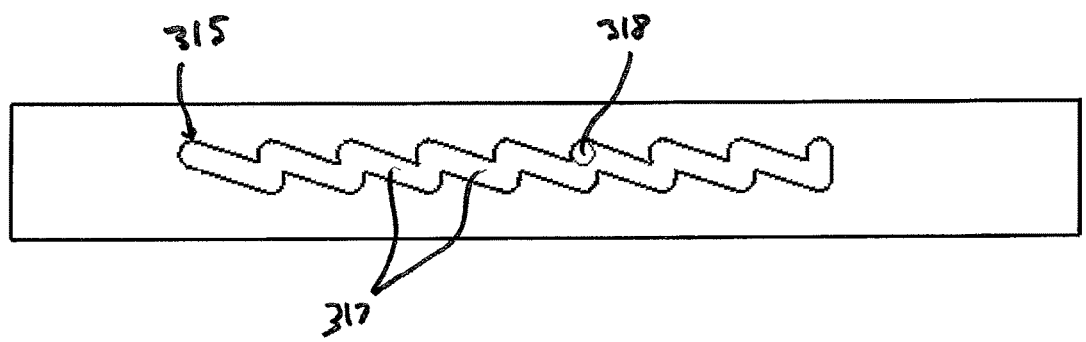
FIG. 30 is a side view of the actuator and actuation rod of FIG. 23, in a third position.
Figure 31:
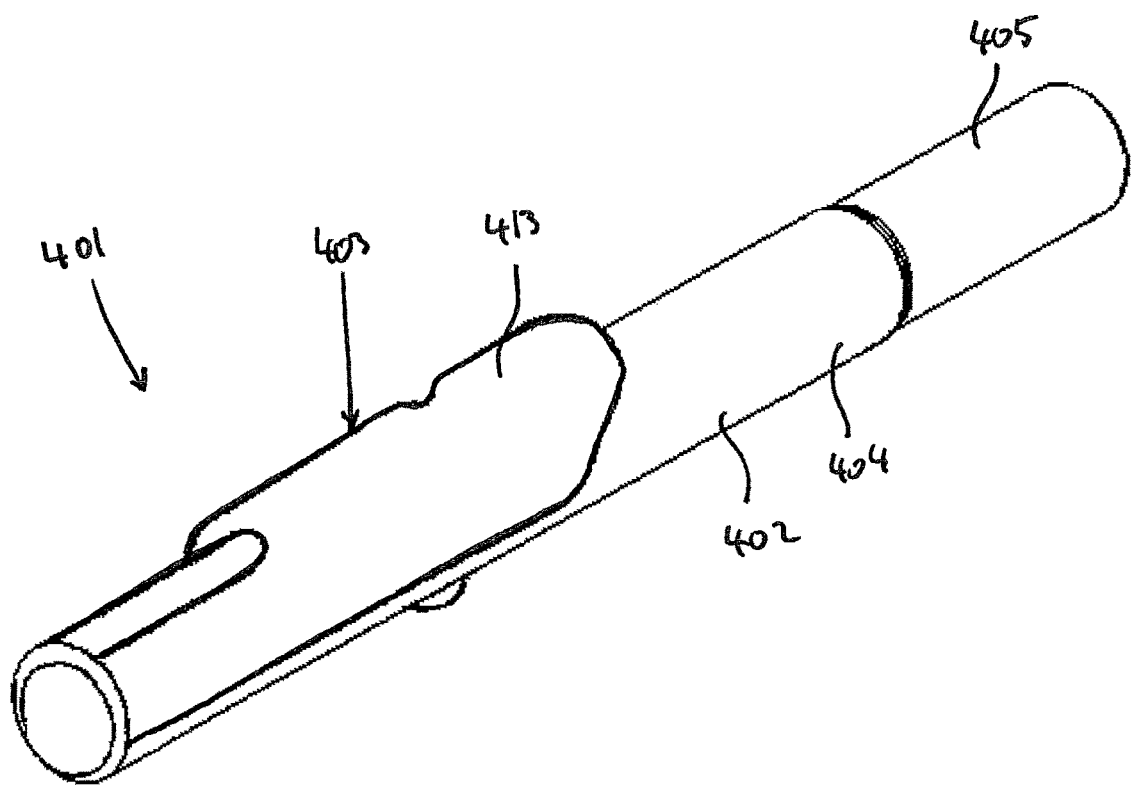
FIG. 31 is a perspective view of a nicotine delivery system of a fifth embodiment.
Figure 32:
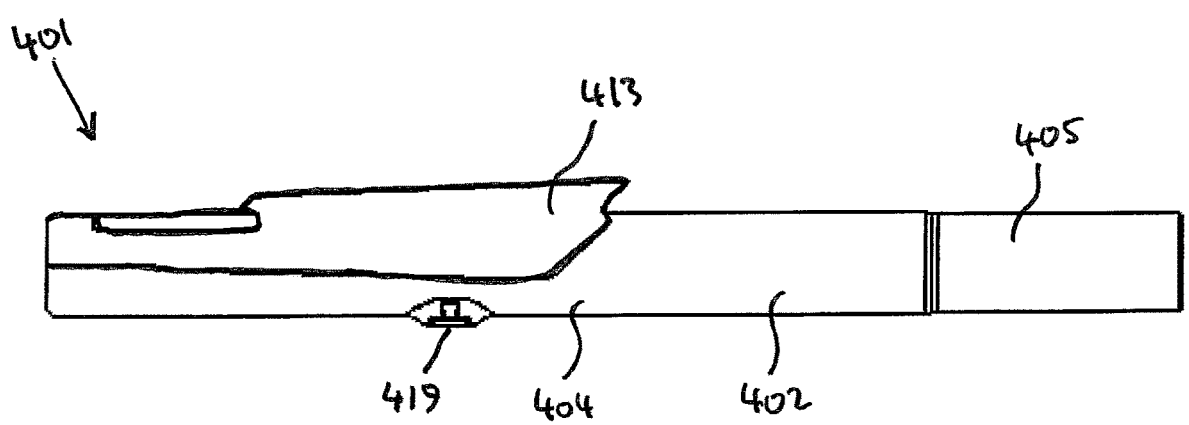
FIG. 32 is a side view of the nicotine delivery system of FIG. 31.
Figure 33:
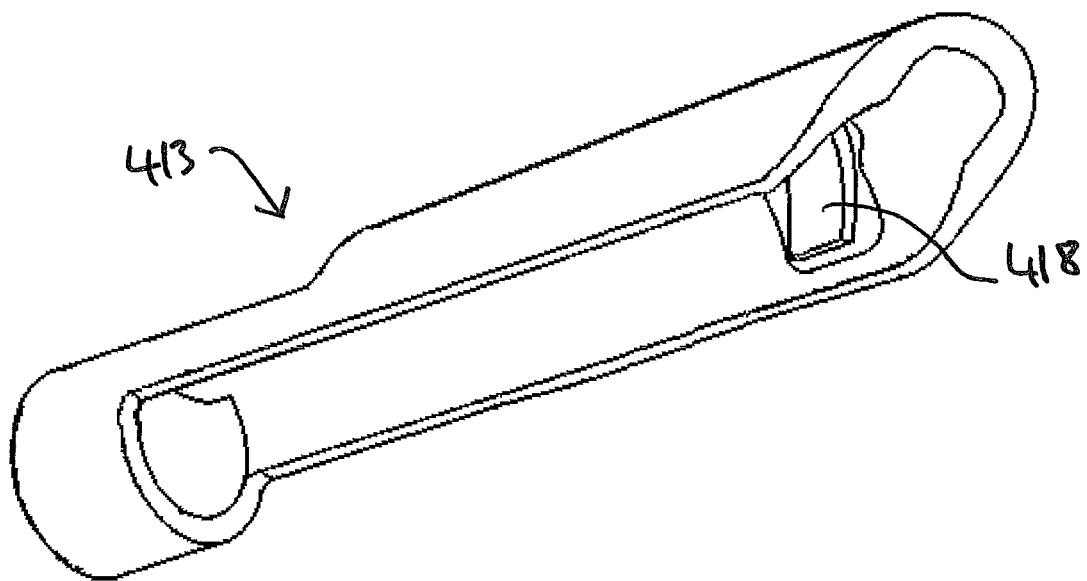
FIG. 33 is a perspective view of an actuator of the nicotine delivery system of FIG. 31.
Figure 34:
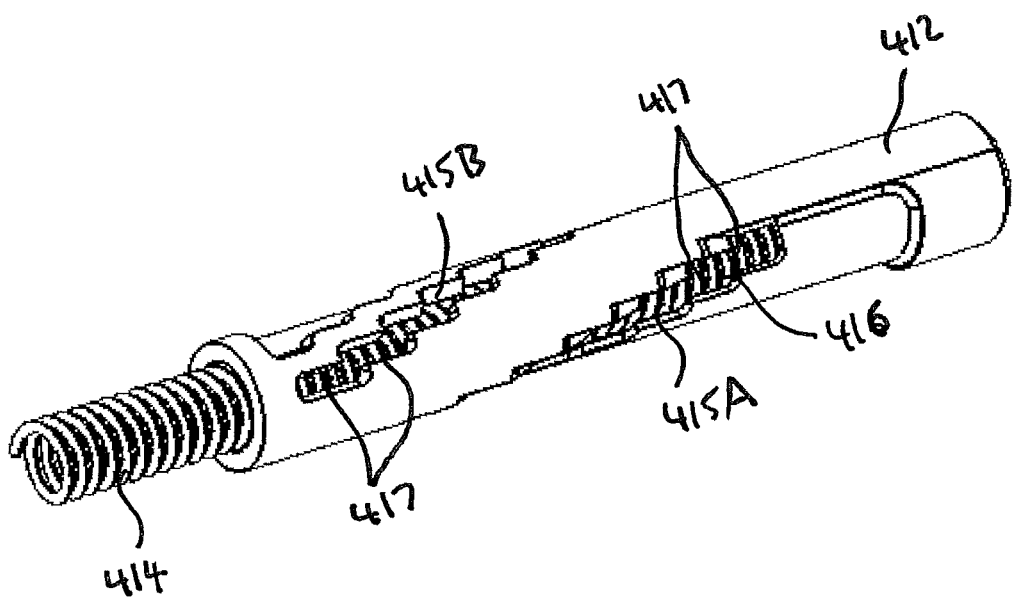
FIG. 34 is a perspective view of an actuation rod and biasing means of the nicotine delivery system of FIG. 31.
Figure 35:
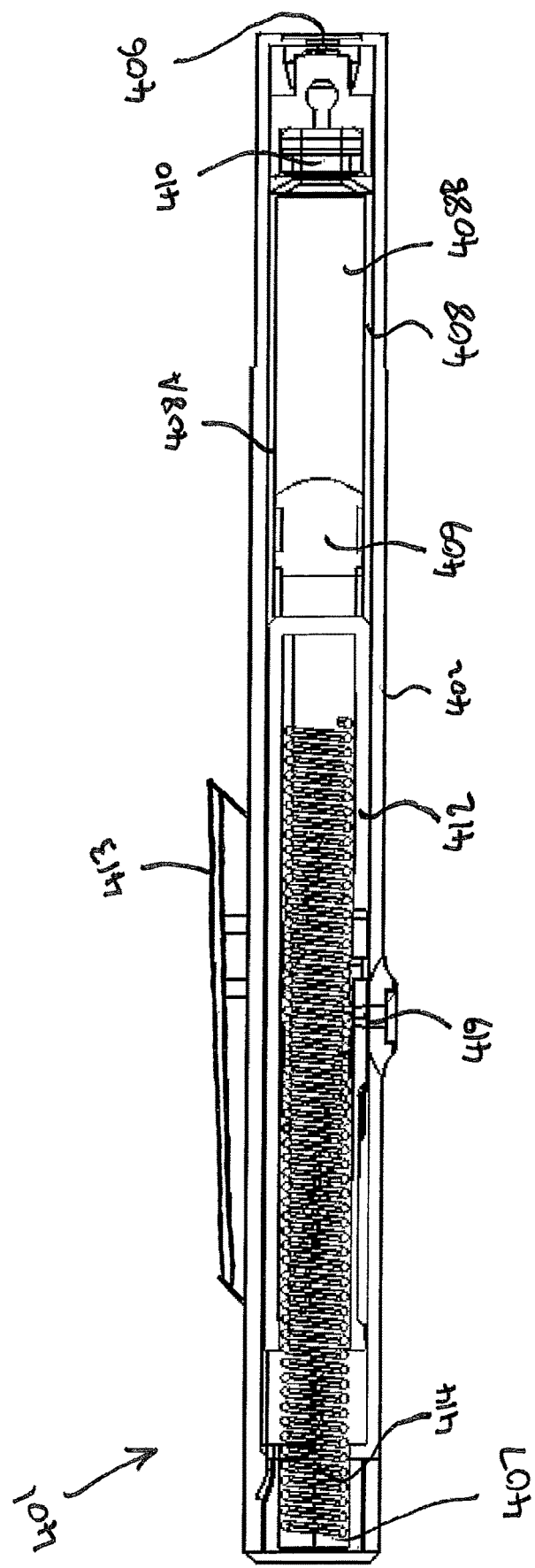
FIG. 35 is a cross-sectional side view of the nicotine delivery system of FIG. 31.

In use, the user applies a force to the actuator 313 to move the actuator 313 into the second position wherein the free end thereof is urged towards the outer housing 302. This will result in the projection 318 being urged in a direction transverse the longitudinal direction of the actuation rod 312 (in the direction shown by arrow 'C' in FIG. 28), resulting in the projection 318 moving into the second end 317B of an adjacent second guide channel 317 (as shown in FIG. 29). In this position, the projection 318 is no longer urged against the stopper edge 317C of the first guide channel 317 and so the actuation rod 312 is free to slide towards the mouthpiece 305 in the longitudinal direction of the outer housing 302 so that the projection 318 moves within the second guide channel 317 (in the direction shown by arrow 'D' in FIG. 29) until it reaches the first end 317A thereof and abuts the stopper edge 317C of the second guide channels 317 (as shown in FIG. 30). As the second guide channel 317 is at an angle with respect to the longitudinal axis of the actuation rod 312, the free end of the actuator 313 is urged away from the outer housing 302 when the projection 318 moves towards the first end 317A of the second guide channel 317 under the force of the biasing means 314, and so the actuator 313 is urged back into its first position. When the projection 318 reaches the first end 317A of the second guide channel 317 it locates against the stopper edge 317C thereof and so the actuation rod 312 is prevented from sliding any further towards the mouthpiece 305 until the user again applies a force to the actuator 313 to push the actuator 313 back into the second position. Thus, the actuation rod 312 is incrementally slidable within the housing upon actuation of the actuator 313 by the user.

As with the first embodiment, a pressure relief valve (not shown) is disposed between the outlet 310 and the outlet channel 306 and is configured to permit the flow of formulation to the outlet channel 306 when the pressure of the formulation in the chamber 308B reaches a pressure set-point. The actuation rod 312 abuts the piston 309 and so when the actuation rod 312 is moved incrementally upon actuation of the actuator 313 the piston 309 is slid within the chamber 308B towards the outlet 310, causing the pressure of the formulation in the chamber 308B to increase above the pressure set-point required to open the pressure relief valve. Therefore, upon actuation of the actuator 313, formulation flows from the outlet 310, through the pressure relief valve, and out of the mouthpiece outlet channel 306. The pressure in the chamber 308B then reduces to below the pressure set-point and the pressure relief valve closes. The actuator 313 may then again be actuated by the user to expel further doses of formulation from the mouthpiece 305 until the piston 309 has been slid relative to the chamber 308B to a position wherein it lies proximate to the outlet 310. As the actuation rod 312 urges the piston 309 relative to the chamber 308B by a predetermined distance upon each actuation of the actuator 313, a set or predetermined amount dosage of formulation is released upon each actuation.

Although in the above described embodiment the actuator 313 is pivotally mounted to the outer housing 302 and rotates relative thereto to move the projections within the cam tracks in a direction transverse the longitudinal direction of the outer housing, in an alternate embodiment (not shown) the actuator comprises a push button that is slidably received in an aperture in the outer housing and slides in a direction transverse the longitudinal direction of the outer housing to move the projections within the cam tracks to release formulation. In yet another embodiment, the actuator comprises a diaphragm, similar in construction to those described in more detail below, and the projections are mounted to the diaphragm so that when the user sucks on the mouthpiece 305, the diaphragm moves in a direction transverse the longitudinal direction of the outer housing to move the projection within the cam tracks to release formulation.

Although in the above described embodiments the actuator comprises first and second projections that are received in first and second cam tracks respectively, in an alternate embodiment (not shown) the second projection and second cam track are omitted.

Referring now to FIGS. 31 to 37, a nicotine delivery system 401 of a fifth embodiment is shown. The nicotine delivery system 401 may be a nicotine delivery system and so may be used as a substitute for cigarette, cigar or like smoking article. The nicotine delivery system 401 comprises an outer housing 402 and an actuating mechanism 403. The outer housing 402 comprises a cylindrical body 404 with a mouthpiece 405 at one end thereof having an outlet channel 406 therein.

An inner chamber 407 is formed in the cylindrical body 404 and has a chamber 408B disposed therein to contain a formulation. The chamber 408B may be defined by the housing itself or it may be a separate, removable, canister 308 having a peripheral wall 408A. The chamber 408B is sealed at one end by a piston 409 that is slidably received therein and the opposing end comprises an outlet 410.

The actuating mechanism 403 comprises an actuation rod 412, an actuator 413, a first biasing means 414 and a stopper pin 419. The actuation rod 412 is disposed in the outer housing 402 and is slidable in the longitudinal direction thereof. The actuator 413 is disposed over a cut-out in the outer housing 402 to enclose the actuation rod 412. The actuation rod 412 comprises a peripheral wall with a chamber formed therein (not shown) that receives the first biasing means 414. First and second cam tracks 415A, 415B are formed on opposing sides of the peripheral wall of the actuation rod 412. The first and second cam tracks 415A, 415B are identical and so only one will be described in detail.

The first cam track 415A comprises a stepped cut-out 416 formed along the length of the peripheral wall of the actuation rod 412. The cut-out 416 comprises a plurality of guide channels 417 that are cut into the peripheral wall of the actuation rod 412 and are arranged so that they extend parallel to the longitudinal axis of the actuation rod 412. Each guide channel 417 comprises a first end 417A that is spaced from the mouthpiece 405 and a second end 417B that is proximate to the mouthpiece 405 when the actuation rod 412 is disposed in the outer housing 402. A side of the first end 417A of each guide channel 417 is formed with a side of the second end 417B of an adjacent guide channel 417 so that the guide channels 417 are arranged sequentially around the periphery of the actuation rod 412 in a stepped formation. The first end 417A of each guide channel 417 comprises a stopper surface 417C that is perpendicular to the longitudinal axis of the actuation rod 412 and faces towards the mouthpiece 405. An actuation surface 417D extends between the first and second ends 417A, 417B of adjacent guide channels 417 and is parallel to the longitudinal axis of the outer housing 402.

Figure 36:
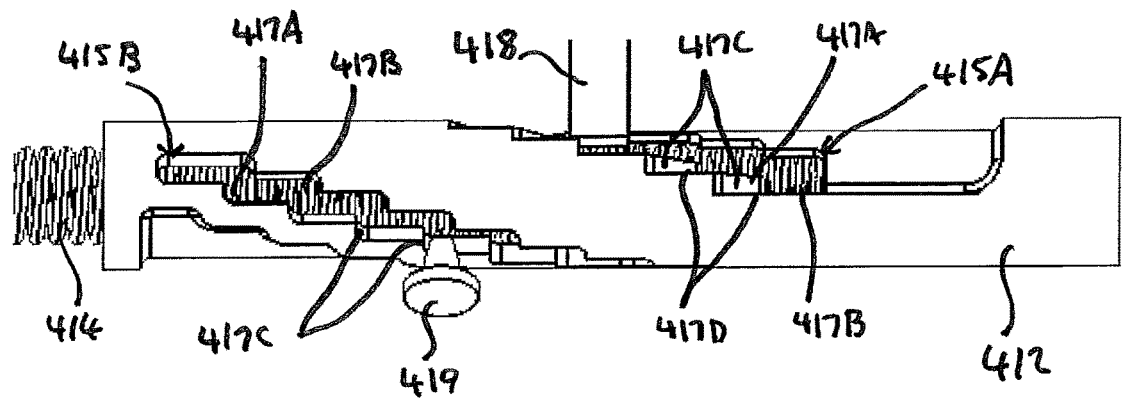
FIG. 36 is a side view of the actuator, biasing means and actuation rod of the nicotine delivery system of FIG. 31, in a first position.

The actuator 413 is pivotally mounted to the outer housing 402 and is rotatable therewith between first and second positions. The actuator 413 comprises a free end and a projection 418 that extends from an inner surface of the actuator 413 in the tangential direction of the peripheral wall of the actuation rod 412. In the first position, the free end of the actuator 413 is spaced from the outer housing 402 and the projection 418 abuts the actuation surface 417D of a first guide channel 417 of the first cam track 415A towards the second end 417B of the first guide channel 417 (as shown in FIG. 36).

The stopper pin 419 extends from an inner surface of the outer housing 402 and is held in a fixed position therewith. The stopper pin 419 is configured to be received in the second cam track 415B of the actuation rod 412. When the actuator 413 is in the first position, the stopper pin 419 is received in the first end 417A of a first guide channel 417 and abuts the stopper surface 417C thereof (as shown in FIG. 36). The first biasing means 414 comprises, for example, a spring or portion of resilient material, and is disposed in the chamber of the actuation rod 412 and is positioned between an end of the actuation rod 412 that is proximate to the mouthpiece 405 and an end portion of the actuator 413 that is spaced from the mouthpiece 405 to urge the actuation rod 412 towards the mouthpiece 405 in the longitudinal direction of the outer housing 402. However, when the actuator 413 is in the first position the stopper surface 417C of the first guide channel 417 is urged against the stopping pin 419 and so the actuation rod 412 is prevented from sliding towards the mouthpiece 405 under the force of the first biasing means 414.

In use, the user applies a force to the actuator 413 to push the actuator 413 into the second position wherein the free end thereof is urged towards the outer housing 402. This will result in the projection 418 being urged in a direction transverse the longitudinal direction of the actuation rod 412 so that the projection 418 is urged against the actuation surface 417D of the first guide channel 417. The actuation rod 412 is free to rotate within the outer housing 402 and therefore as the projection 418 is urged against the first actuation surface 417D the actuation rod 412 will rotate so that the stopper pin 419 is moved within the second cam track 415B into the second end 417B of a second guide channel 417 that is adjacent to the first guide channel 417. In this position, the stopper pin 419 no longer abuts a stopper surface 417C and so the actuation rod 412 is free to slide towards the mouthpiece 405 in the longitudinal direction of the outer housing 402 under the force of the first biasing means 414 so that the stopper pin 419 moves within the second guide channel 417 of the second cam track 415B towards the first end 417A thereof and the projection 418 slides along the actuation surface 417D of the first guide channel 417 of the first cam track 415A towards the first end 417B thereof until the projection 418 abuts the stopper surface 417C thereof.

Figure 37:
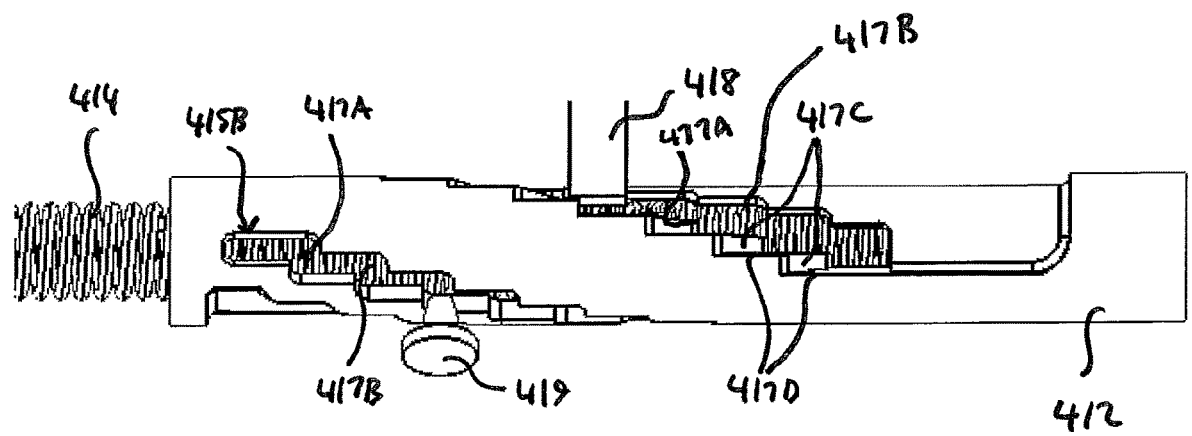
FIG. 37 is a side view of the actuator, biasing means and actuation rod of the nicotine delivery system of FIG. 31, in a second position.
Figure 38:
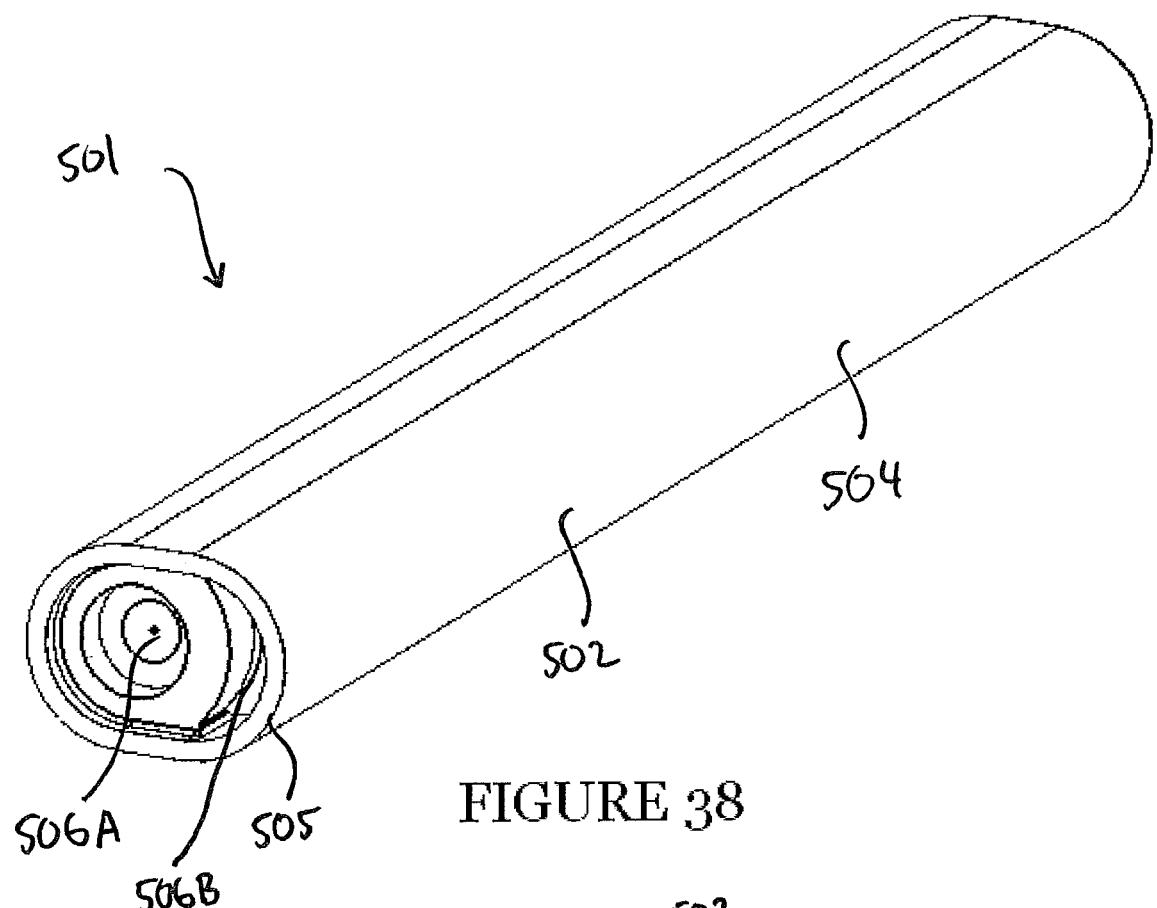
FIG. 38 is a perspective view of a nicotine delivery system of a sixth embodiment.
Figure 39:
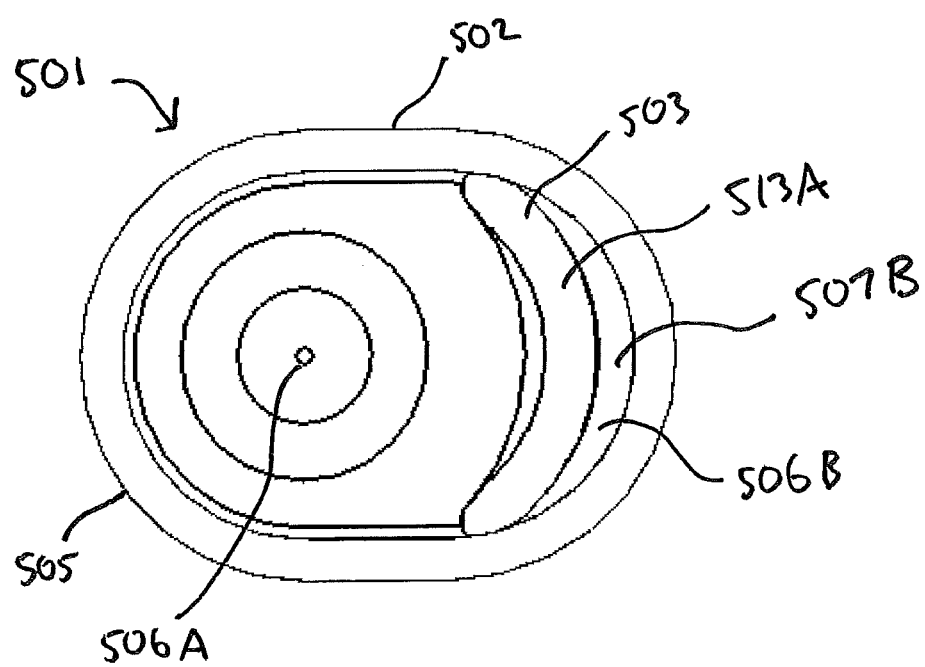
FIG. 39 is a front view of the nicotine delivery system of FIG. 38.
Figure 40:
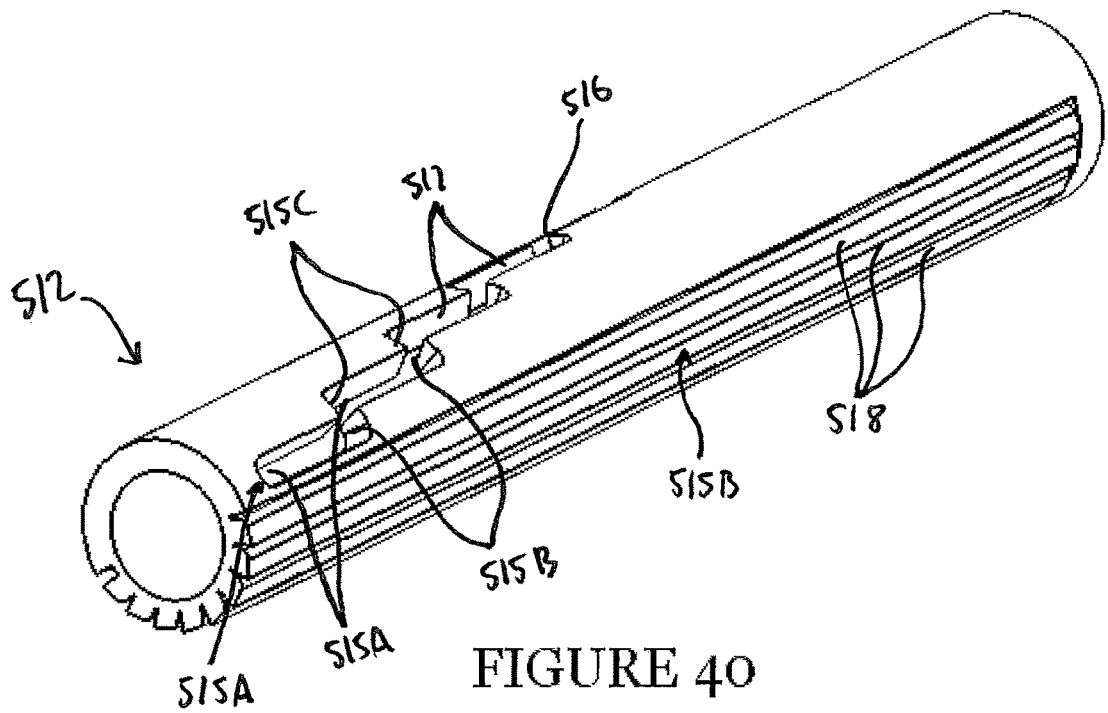
FIG. 40 is a perspective view of an actuation rod of the nicotine delivery system of FIG. 38.
Figure 41:
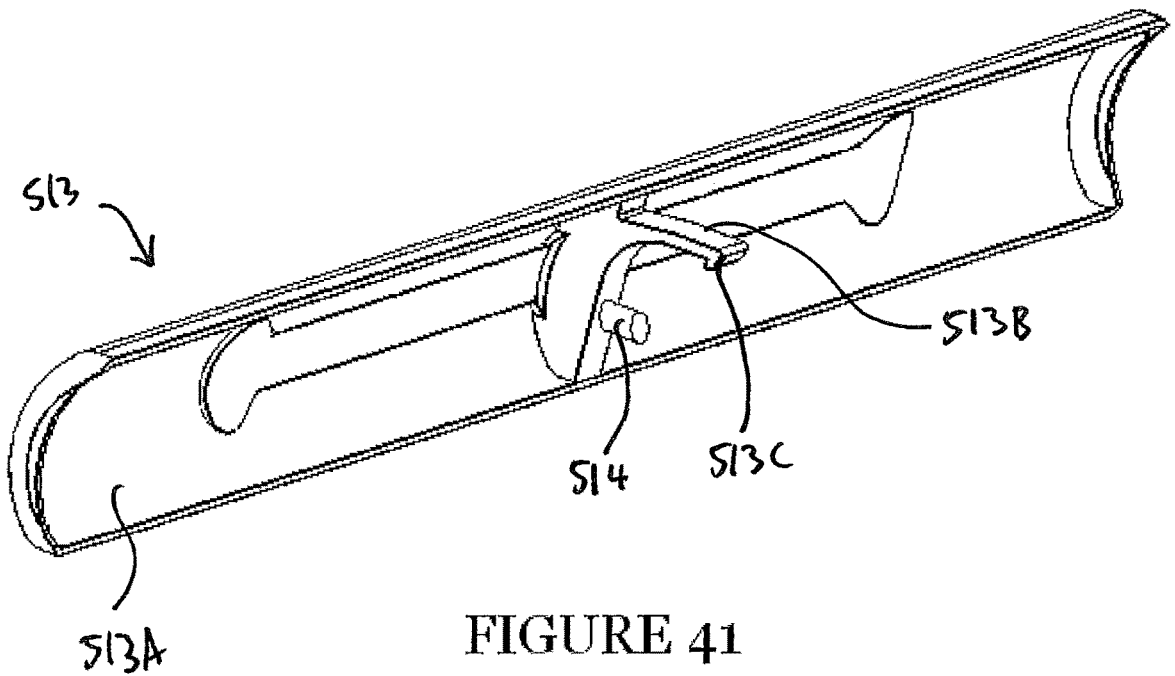
FIG. 41 is a perspective view of a diaphragm of the nicotine delivery system of FIG. 38.
Figure 42:
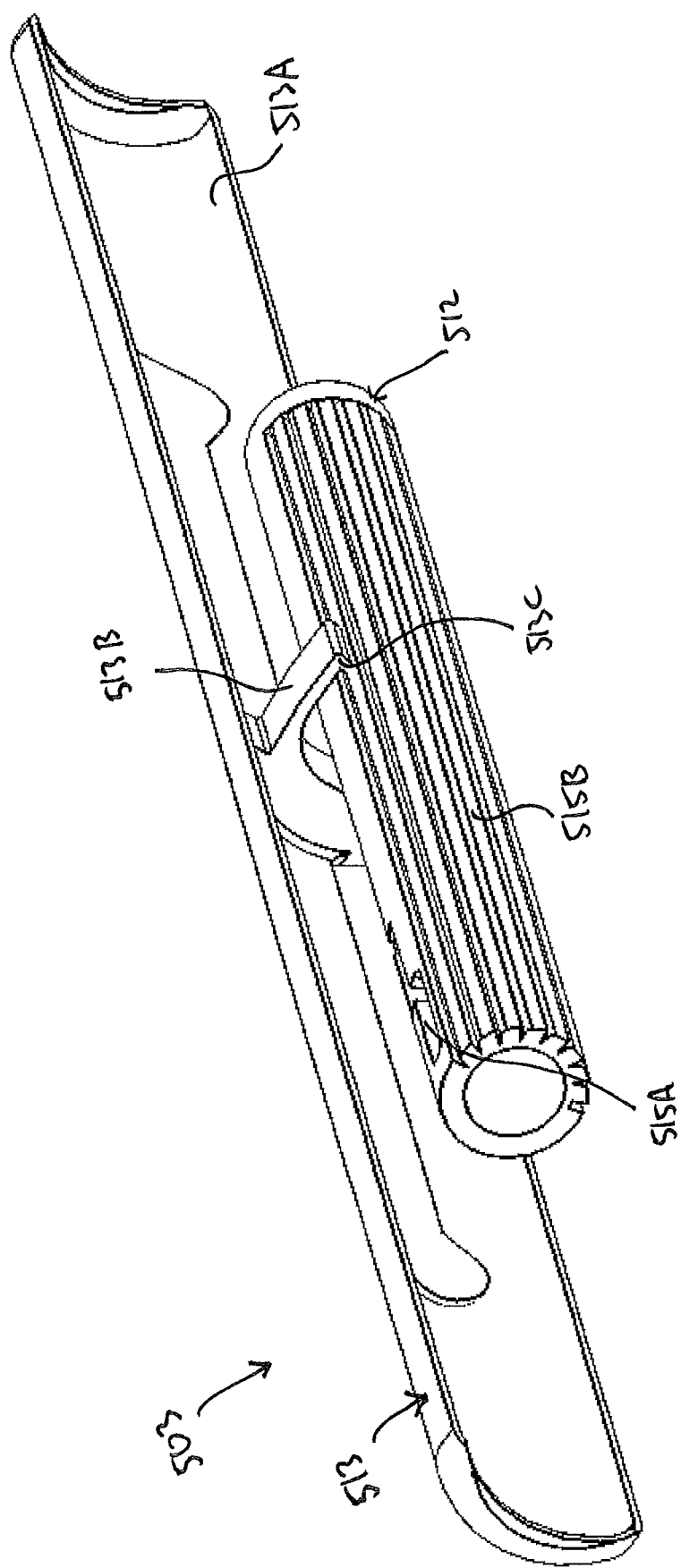
FIG. 42 is a perspective view of the actuation rod and diaphragm of the nicotine delivery system of FIG. 38.

A second biasing means (not shown) comprising, for example, a spring or portion of resilient material, is positioned between the actuator 413 and the valve housing 402 and biases the actuator 413 into the first position, wherein the free end of the actuator 413 is spaced from the outer housing 402. Therefore, when the user releases the actuator 413 so that a force is no longer exerted thereon by the user, the free end of the actuator 413 is urged away from the outer housing 402 and the projection 418 moves away from the actuation surface 417D of the first guide channel 417 so that the projection 418 is no longer urged against the stopper surface 417C of the first guide channel 417. The actuation rod 412 is then slid towards the mouthpiece 405 under the force of the first biasing means 414 until the stopper pin 419 abuts the stopper surface 417C of the second guide channel 417 of the second cam track 415B (as shown in FIG. 37). In this position, the projection 418 is urged against the actuation surface 417D of a second guide channel 417, adjacent to the first guide channel 417, and the actuator 413 may be actuated again by the user to further rotate the actuation rod 412 to again move the actuation rod 412 towards the mouthpiece 405 in the manner previously described. Thus, the actuation rod 412 is incrementally slidable within the outer housing 402 upon actuation of the actuator 413 by the user.

As with the first embodiment, a pressure relief valve (not shown) is disposed between the outlet 410 and the outlet channel 406 and is configured to permit the flow of formulation from the chamber 408B to the outlet channel 406 when the pressure of the formulation in the chamber 408B reaches a pressure set-point. The actuation rod 412 abuts the piston 409 and so when the actuation rod 412 is moved incrementally upon actuation of the actuator 413 the piston 409 is slid within the chamber 408B towards the outlet 410, causing the pressure of the formulation in the chamber 408B to increase above the pressure set-point required to open the pressure relief valve. Therefore, upon actuation of the actuator 413, formulation flows from the outlet 410, through the pressure relief valve, and out of the mouthpiece outlet channel 406. The pressure in the chamber 408B then reduces to below the pressure set-point and the pressure relief valve closes. The actuator 413 may then again be actuated by the user to expel further doses of formulation from the mouthpiece 405 until the piston 409 has been slid relative to the chamber 408B to a position wherein it lies proximate to the outlet 410. As the actuation rod 412 urges the piston 409 relative to the chamber 408B by a predetermined distance upon each actuation of the actuator 413, a set amount dosage of formulation is released upon each actuation.

Although in the above described embodiment the actuator 413 is pivotally mounted to the outer housing 402 and rotates relative thereto to move the projection 418 in a direction transverse the longitudinal direction of the outer housing 402 to apply a force to an actuation surface 417D to rotate the actuation rod 412, in an alternate embodiment (not shown) the actuator comprises a push button that is slidably received in an aperture in the outer housing and slides in a direction transverse the longitudinal direction of the outer housing to move the projection towards an actuation surface to rotate the actuation rod. In yet another embodiment, the actuator comprises a diaphragm, similar in construction to those described in more detail below, and the projection is mounted to the diaphragm so that when the user sucks on the mouthpiece 405, the diaphragm moves in a direction transverse the longitudinal direction of the outer housing to move the projection towards the actuation surface to rotate the actuation rod.

Referring now to FIGS. 38 to 46, a nicotine delivery system 501 of a sixth embodiment is shown. The nicotine delivery system 501 comprises an outer housing 502 and an actuating mechanism 503. The outer housing 502 comprises an elliptical cylinder shaped body 504 with a mouthpiece 505 at one end thereof having an outlet channel 506A and a suction channel 506B therein.

The actuating mechanism 503 comprises an actuation rod 512, an actuator 513, a biasing means (not shown) and a stopper pin 514. The actuator 513 comprises a diaphragm 513A with a ratchet peg 513B attached thereto. The diaphragm 513A is disposed in an inner space 507 in the body 504 and partitions said space 507 into first and second compartments 507A, 507B. The diaphragm 513A is manufactured from a flexible material, for example, rubber or plastic. The diaphragm 513A seals the first compartment 507A from the second compartment 507B and a chamber 508B is disposed in the first compartment 507A that contains a formulation, and which may be defined by the housing 502 itself or may be a separate, removable, canister 508 having a peripheral wall 508A. The chamber 508B is sealed at one end of by a piston 509 that is slidably received in the chamber 508B and has an outlet 510 at the opposing end.

The actuation rod 512 is disposed in the first compartment 507A and is slidable in the longitudinal direction of the outer housing 502. The actuation rod 512 comprises a peripheral wall with a chamber formed therein (not shown) that receives the biasing means. A cam track 515A and a ratchet track 515B are formed in the peripheral wall of the actuation rod 512.

The cam track 515A comprises a stepped cut-out 516 formed along the length of the peripheral wall of the actuation rod 512. The cut-out 516 comprises a plurality of guide channels 517 that are cut into the peripheral wall of the actuation rod 512 and are arranged so that they extend parallel to the longitudinal axis of the actuation rod 512. Each guide channel 517 comprises a first end 517A that is spaced from the mouthpiece 505 and a second end 517B that is proximate to the mouthpiece 505 when the actuation rod 512 is disposed in the outer housing 502. A side of the first end 517A of each guide channel 517 is formed with a side of the second end 517B of an adjacent guide channel 517 so that the guide channels 517 are arranged sequentially around the periphery of the actuation rod 512 in a stepped formation. The first end 517A of each guide channel 517 comprises a stopper edge 517C that is perpendicular to the longitudinal axis of the actuation rod 512 and faces towards the mouthpiece 505.

The ratchet track 515B comprises a plurality of ratchet teeth 518 formed around the opposite side of the peripheral wall of the actuation rod 512 to the cam track 515A. Each tooth 518 has an actuation surface 518A that faces in a tangential direction of the actuation rod 512, and a connecting surface 518B that is angled with respect to said tangential direction and connects the actuation surfaces 518A of adjacent teeth 518 to form a saw-tooth shaped configuration.

Figure 43:
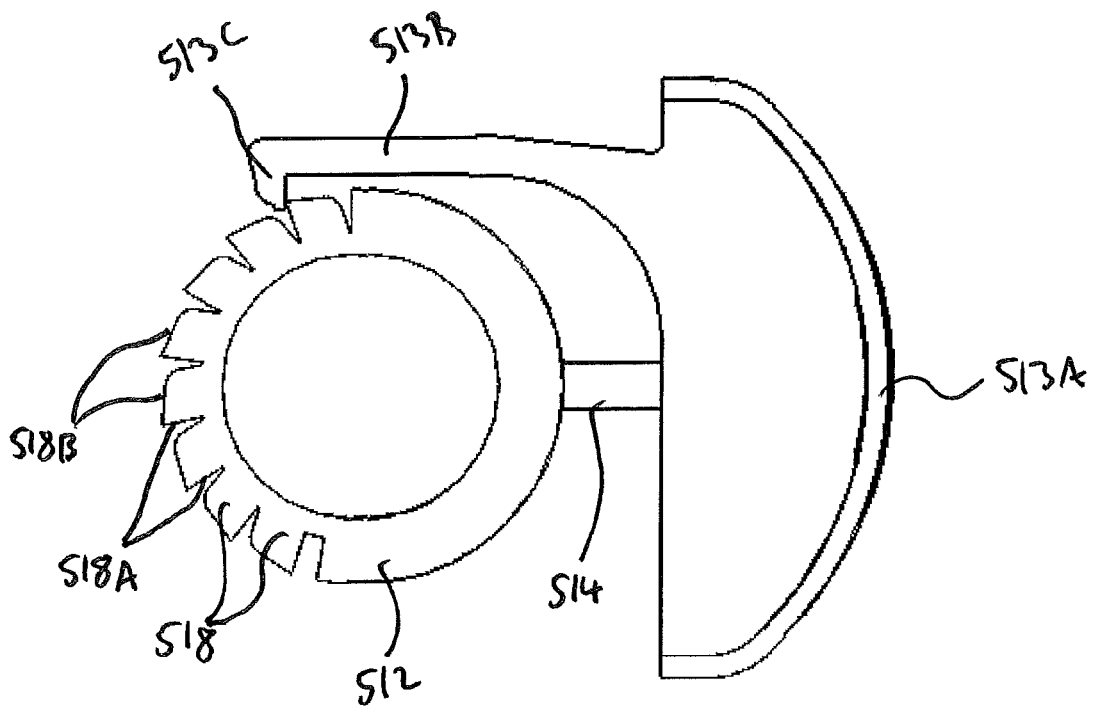
FIG. 43 is a front view of the actuation rod and diaphragm of the nicotine delivery system of FIG. 38, in a first position.
Figure 44:
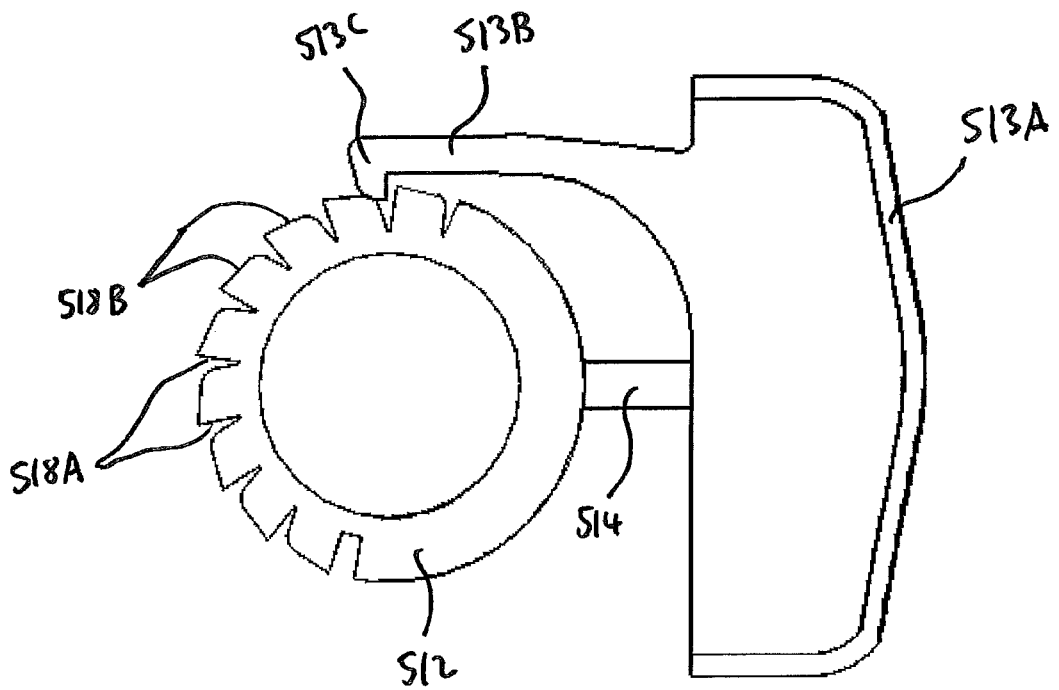
FIG. 44 is a front view of the actuation rod and diaphragm of the nicotine delivery system of FIG. 38, in a second position.
Figure 45:
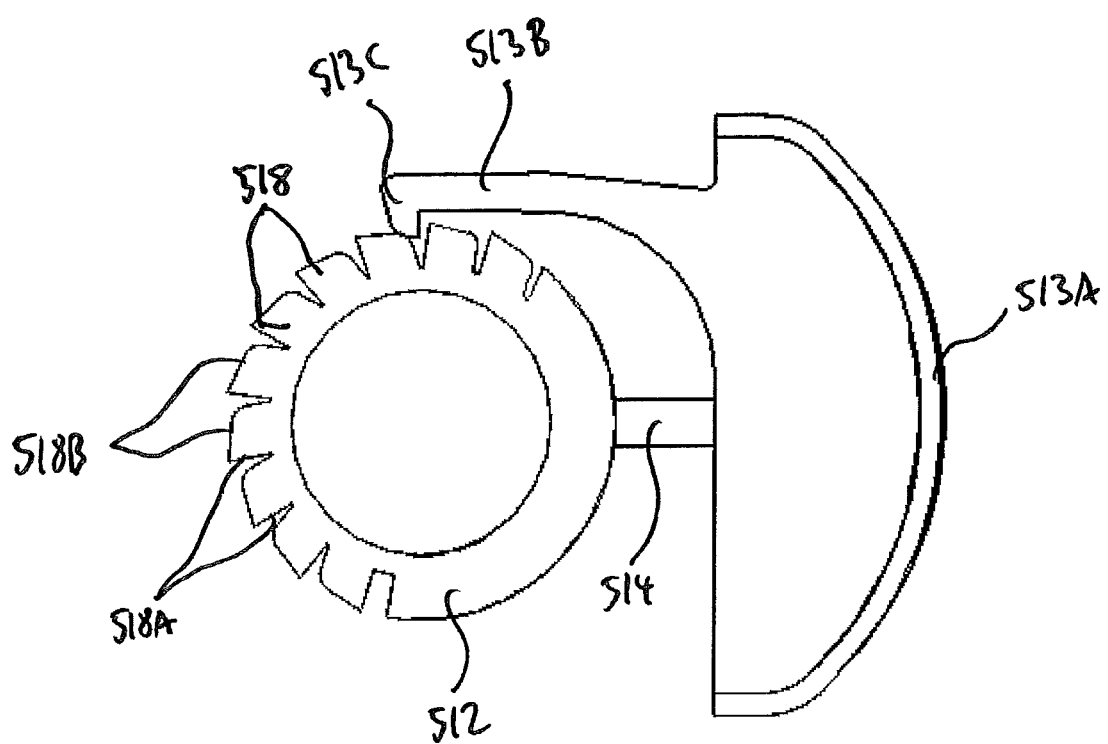
FIG. 45 is a front view of the actuation rod and diaphragm of the nicotine delivery system of FIG. 38, in a third position.
Figure 46:
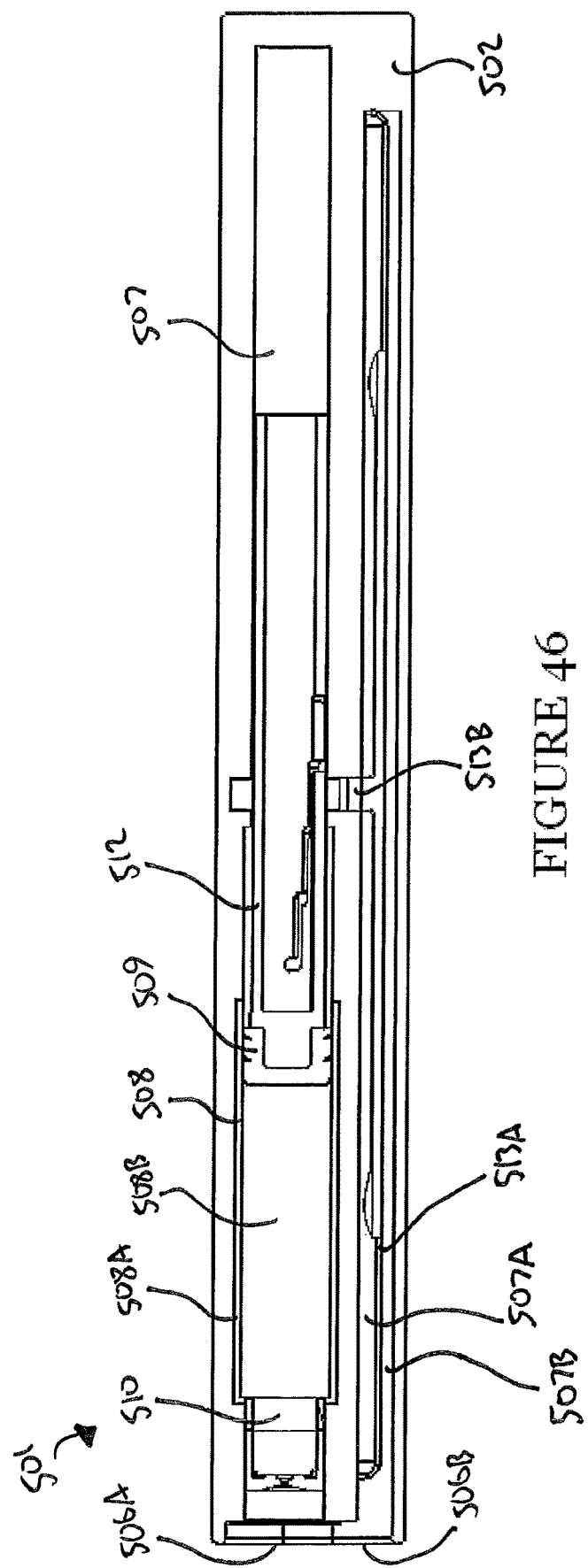
FIG. 46 is a cross-sectional side view of the nicotine delivery system of FIG. 38.
Figure 47:
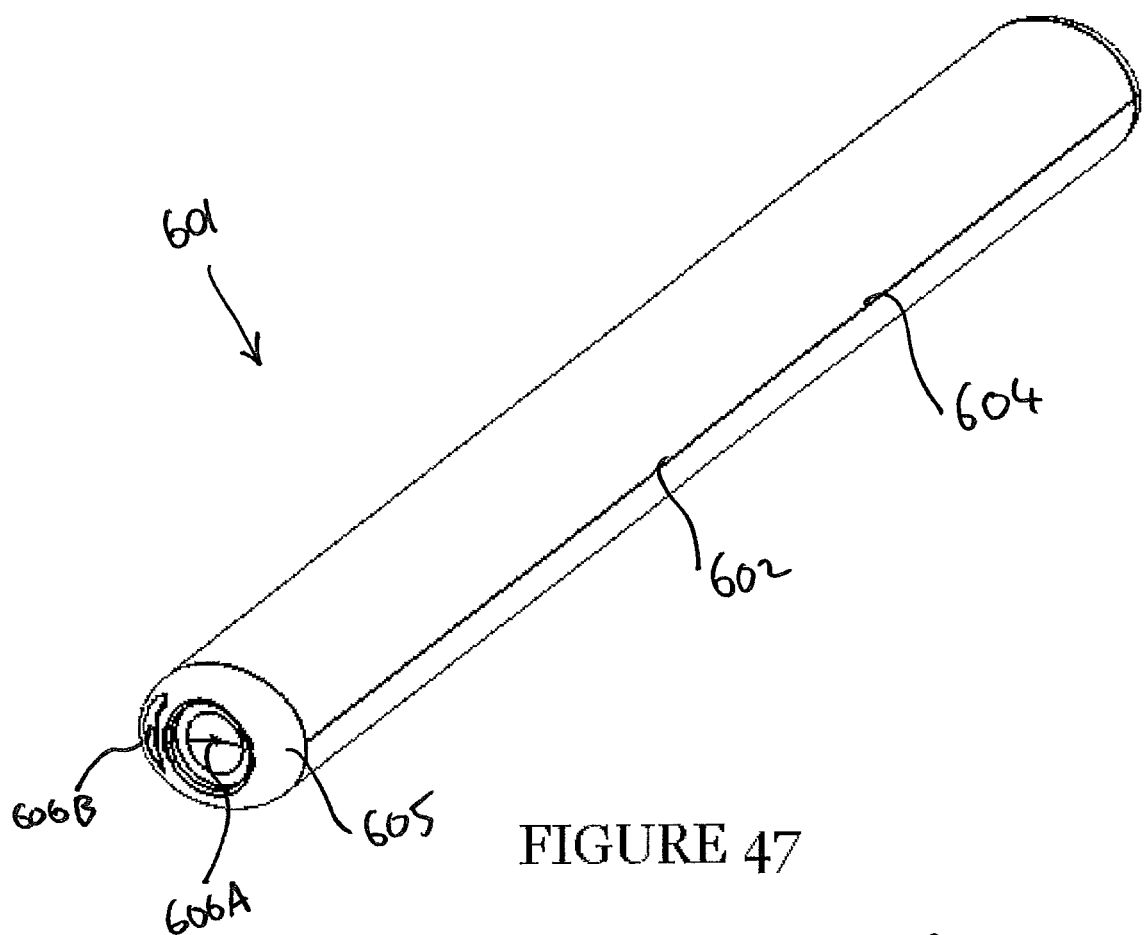
FIG. 47 is a perspective view of a nicotine delivery system of a seventh embodiment.
Figure 48:
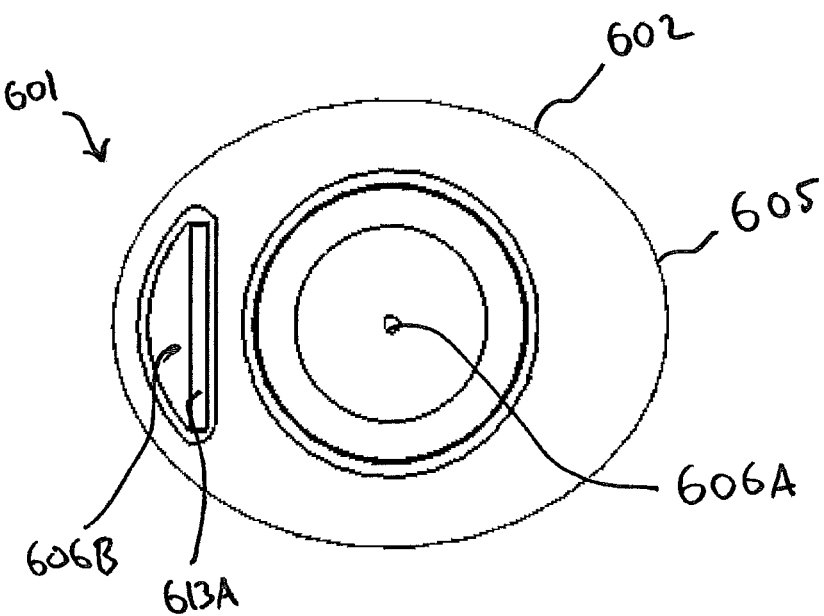
FIG. 48 is a front view of the nicotine delivery system of FIG. 47.
Figure 49:
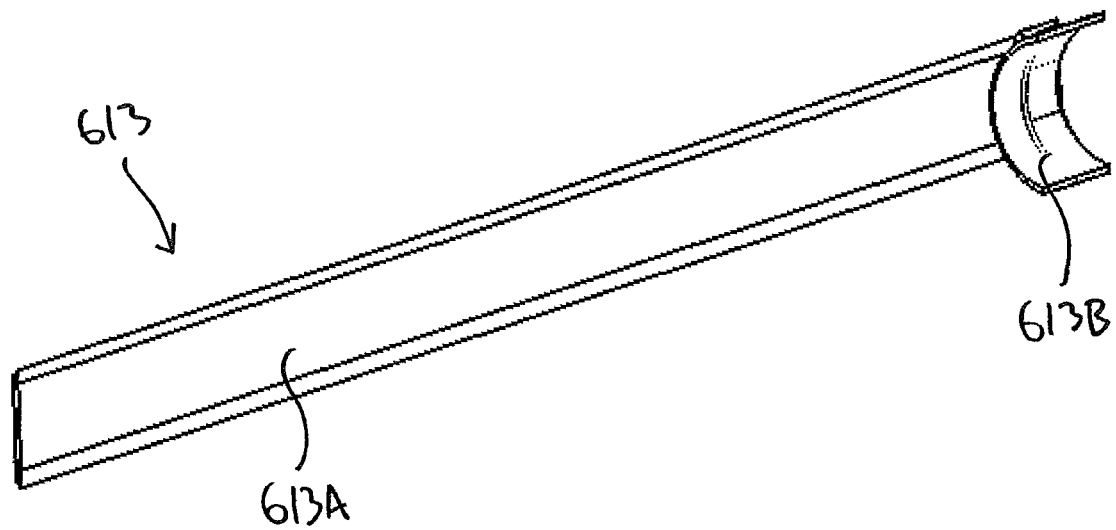
FIG. 49 is a perspective view of the diaphragm of the nicotine delivery system of FIG. 47.
Figure 50:
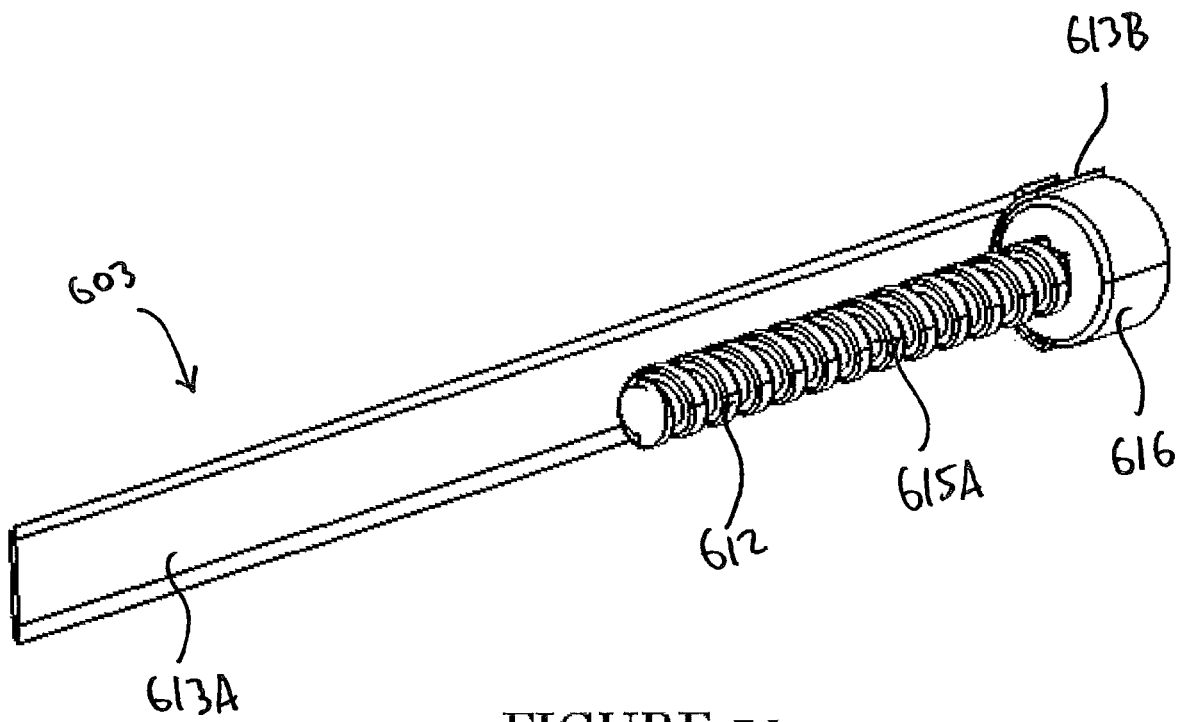
FIG. 50 is a perspective view of the diaphragm, an actuation rod and a friction wheel of the nicotine delivery system of FIG. 47.
Figure 51:
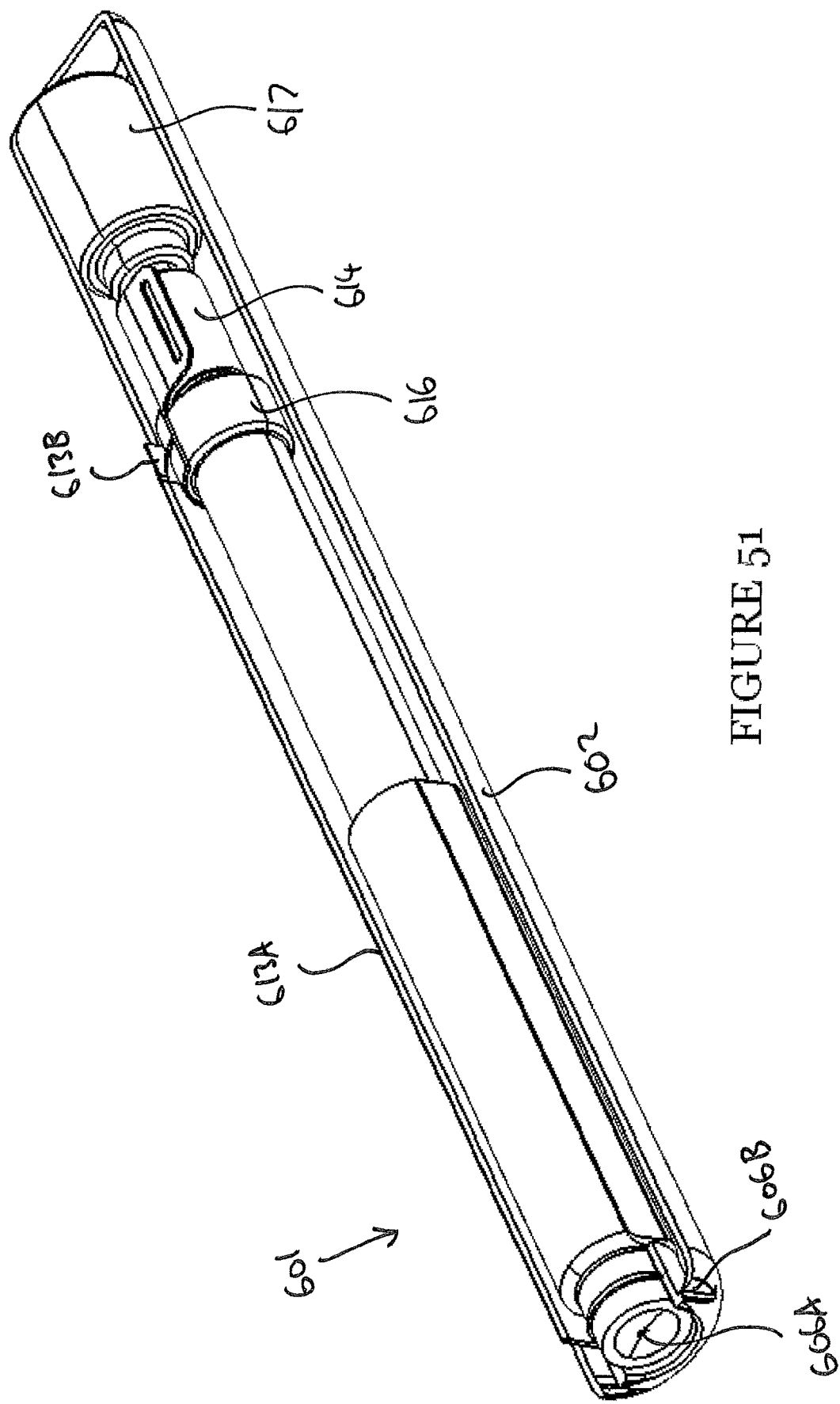
FIG. 51 is a perspective view of part of the nicotine delivery system of FIG. 47.
Figure 52:
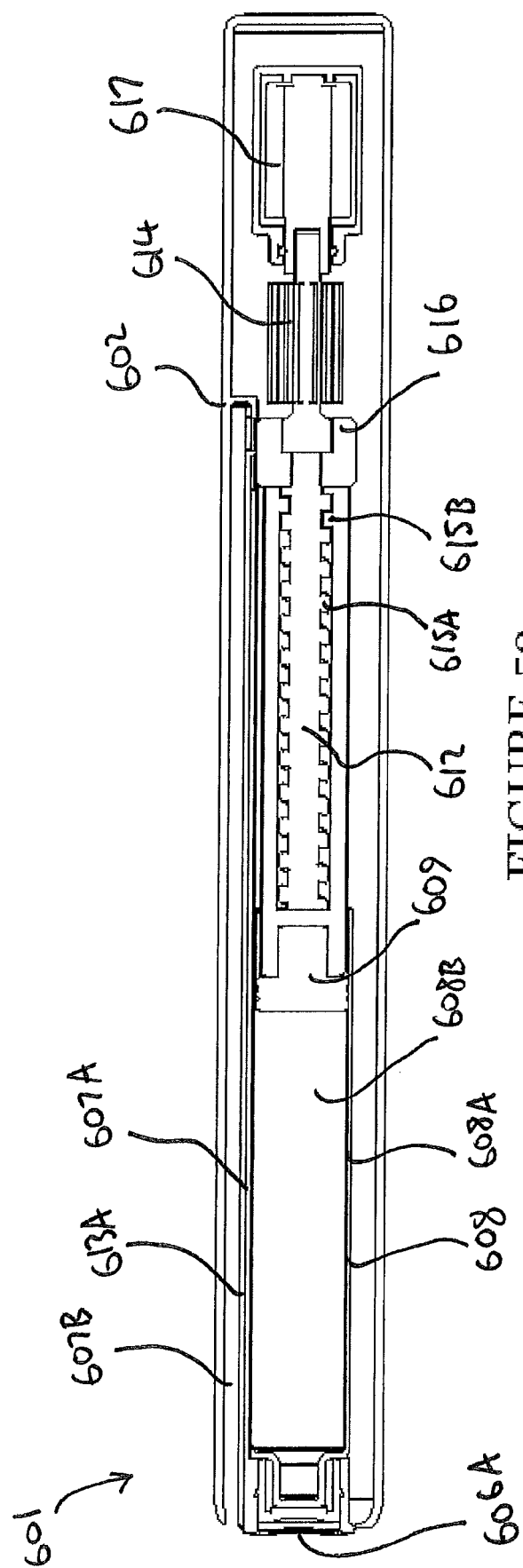
FIG. 52 is a cross-sectional side view of the nicotine delivery system of FIG. 47.
Figure 53:
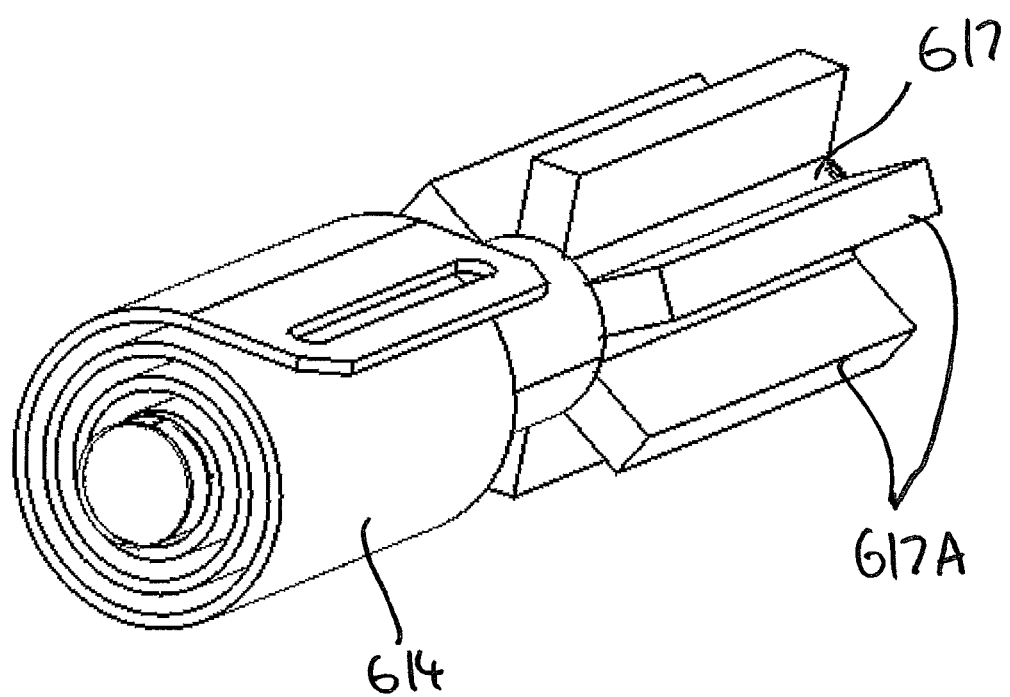
FIG. 53 is a perspective view of a biasing means and a damper of the nicotine delivery system of FIG. 47.

The inside of the first compartment 507A is sealed from the inside of chamber of the canister 508 and the outlet channel 506A and the inside of the second compartment 507B is fluidly communicated with the end of the mouthpiece 505 by the suction channel 506B. Therefore, when the user sucks on the mouthpiece 505 to draw formulation through the outlet channel 506A, air in the second compartment 507B is sucked through the suction channel 506B and therefore the pressure in the second compartment 507B reduces so that it is less than the pressure in the first compartment 507A. This causes the diaphragm 513A to be urged away from the actuation rod 512 so that it deforms and the volume in the second chamber 507B decreases. The ratchet peg 513B comprises a rigid member that extends from the surface of the diaphragm 513A and comprises a projection 513C that is configured to engage with the actuation surface 518A of a first ratchet tooth 518 (as shown in FIG. 43). Therefore, when the diaphragm 513A is urged away from actuation rod 512 under the force of the pressure drop in the second compartment 507B, the projection 513C of the ratchet peg 513B is urged against the actuation surface 518A of the first ratchet tooth 518 and the actuation rod 512 is urged to rotate (as shown in FIG. 44). When the user removes the nicotine delivery system 501 from their mouth, air flows back into the second compartment 507B, via the suction channel 506B. The diaphragm 513A is manufactured from a resilient material and is configured so that when the air flows back into the second compartment 507B the diaphragm 513A will move back towards the actuation rod 512 and the projection 513C of the ratchet peg 513B will move over the connecting surface 518B of the first ratchet tooth 518 until it abuts the actuation surface 518A of an adjacent second ratchet tooth 518 (as shown in FIG. 45).

The stopper pin 514 extends from an inner surface of the ratchet peg 513B and is held if a fixed position therewith. The stopper pin 514 is configured to be received in the cam track 515A of the actuation rod 512. When the actuator 513 is in the first position, the stopper pin 514 is received in the first end 517A of a first guide channel 517 and abuts the stopper edge 517C thereof. The first biasing means comprises, for example, a spring or portion of resilient material, and is disposed in the chamber of the actuation rod 512 and is positioned between an end of the actuation rod 512 that is proximate to the mouthpiece 505 and an end portion of the actuator 513 that is spaced from the mouthpiece 505 to urge the actuation rod 512 towards the mouthpiece 505 in the longitudinal direction of the outer housing 502. However, when the actuator 513 is in the first position the stopper edge 517C of the first guide channel 517 is urged against the stopping pin 514 and so the actuation rod 512 is prevented from sliding towards the mouthpiece 505 under the force of the first biasing means. In use, the actuation rod 512 rotates relative to the outer housing 502 in the manner previously described, resulting in the stopper pin 514 being moved within the cam track 515A into the second end 517B of a second guide channel 517 that is adjacent to the first guide channel 517. In this position, the stopper pin 519 no longer abuts a stopper edge 517C and so the actuation rod 512 is free to slide towards the mouthpiece 505 in the longitudinal direction of the outer housing 502 under the force of the first biasing means so that the stopper pin 514 moves within the second guide channel 517 towards the first end 517A thereof until the stopper pin 514 abuts the stopper edge 517C of the second guide channel 517. Thus, the actuation rod 512 is incrementally slidable within the outer housing 502 upon actuation of the actuator 513, in a direction transverse the longitudinal direction of the outer housing 502.

As with the first embodiment, a pressure relief valve (not shown) is disposed between the outlet 510 and the outlet channel 506A and is configured to permit the flow of formulation from the chamber 508B to the outlet channel 506A when the pressure of the formulation in the chamber 508B reaches a pressure set-point. The actuation rod 512 abuts the piston 509 and so when the actuation rod 512 is moved incrementally upon actuation of the actuator 513 the piston 509 is slid within the chamber 508B towards the outlet 510, causing the pressure of the formulation in the chamber 508B to increase above the pressure set-point required to open the pressure relief valve. Therefore, upon actuation of the actuator 513, formulation flows from the outlet 510, through the pressure relief valve, and out of the mouthpiece outlet channel 506A. The pressure in the chamber 508B then reduces to below the pressure set-point and the pressure relief valve closes. The actuator 513 may then again be actuated by the user sucking on the mouthpiece 505 to expel further doses of formulation from the mouthpiece 505 until the piston 509 has been slid relative to the chamber 508B to a position wherein it lies proximate to the outlet 510. As the actuation rod 512 urges the piston 509 relative to the chamber 508B by a predetermined distance upon each actuation of the actuator 513, a set amount dosage of formulation is released upon each actuation. Therefore, the user nicotine delivery system 501 may be configured to release a safe dosage of formulation upon each actuation.

Although in the above described embodiment the diaphragm 513A is manufactured from a resilient material so that it may be urged towards the actuation rod 512 when pressure in the second compartment 507B equalizes with the pressure in the first compartment 507A, in an alternate embodiment (not shown) the diaphragm may instead be urged towards the actuation rod by a biasing member, for example, a spring or portion of resilient material, that is positioned in the first or second compartments 507A, 507B between the outer housing 502 and the diaphragm 513A. In one embodiment, the diaphragm 513A is pivotally mounted to the outer housing 502 at an end thereof and pivots in a direction transverse the longitudinal direction of the outer housing 502.

Although in the above described embodiment, the stopping pin 514 is provided the inner surface of the ratchet peg 513B, in an alternate embodiment (not shown) the stopping pin 514 is provided on an inside surface of the outer housing 502.

Although in the above described embodiment the actuator 513 is configured so that the diaphragm 513A is urged away from the actuation rod 512, in an alternate embodiment (not shown) the diaphragm 513A is configured to be urged towards the actuation rod 512. For example, the second compartment 507B may be sealed and instead the inside of the first compartment 507A is fluidly communicated with the suction channel 506B so that when the user sucks on the mouthpiece 505, the pressure in the first compartment 507A becomes less than the pressure in the second compartment 507B to deform the diaphragm 513A so that it is urged towards the actuation rod 512. In such an embodiment, the ratchet peg 513B and ratchet teeth 518 are configured so that the actuation rod 512 is rotated when the diaphragm 513A is moved towards the actuation rod 512.

Although in the above described the diaphragm 513A is manufactured from a resilient material that provides a biasing force to urge the diaphragm 513A towards the actuation rod 512 when the user removes the mouthpiece 505 from their mouth, it should be recognized that the biasing force may be provided solely by the pressure differences between the first and second compartments 507A, 507B. For example, if the first compartment 507A is sealed from the atmosphere the pressures in the first and second compartments 507A, 507B will be equal until the user sucks on the mouthpiece 505 to draw air out of the second compartment 507B, via the suction channel 506B, whereupon the diaphragm 513A will be urged away from the actuation rod 512 so that the volume of the second compartment 507A decreases. This will result in the volume of the first compartment 507A increasing and the pressure therein decreasing. Therefore, when the user removes the mouthpiece 505 from their mouth so that air may pass into the second compartment 507B, the diaphragm 513A will be urged back towards the actuation rod 512 so that the volume of the first compartment 507A reduces until the pressures in the first and second compartments 507A, 507B equalize. In alternative embodiments, the biasing force may be provided solely by the resilience of the diaphragm or a biasing member, in which case a ventilation aperture (not shown) may be provided in the outer housing 502 to fluidly communicate the inside of the first compartment 507A with the atmosphere to facilitate movement of the diaphragm 513A.

Although in the above described embodiment the actuator 513 comprises a diaphragm 513A that is actuated upon the user sucking on the mouthpiece 505, in an alternate embodiment the diaphragm 513A is omitted and replaced with an actuator of the type described in the previous embodiments.

For example, the actuator may comprise a push button that is connected to the ratchet peg 513B and is configured to urge the ratchet peg 513B to rotate the piston rod 512 to release formulation upon actuation by the user.

Referring now to FIGS. 47 to 53, a nicotine delivery system 601 of a seventh embodiment is shown. The nicotine delivery system 601 may be used as a substitute for cigarette, cigar or like smoking article. The nicotine delivery system 601 comprises an outer housing 602 and an actuating mechanism 603. The outer housing 602 comprises an elliptical cylinder shaped body 604 with a mouthpiece 605 at one end thereof having an outlet channel 606A and a suction channel 606B.

The actuating mechanism 603 comprises an actuation rod 612, an actuator 613 and a biasing means 614. The actuator 613 comprises a diaphragm 613A with a friction pad 613B attached thereto. The diaphragm 613A is disposed in an inner space 607 in the body 604 and partitions said space 607 into first and second compartments 607A, 607B. The diaphragm 613A is manufactured from a flexible material, for example, rubber or plastic. The diaphragm 613A seals the first compartment 607A from the second compartment 607B and a chamber 608B is disposed in the first compartment 607A that may be formed integrally with the housing 602 or may be a separate, removable component having a peripheral wall 608A. The chamber 608B is sealed at one end by a piston 609 that is slidably received in the chamber 608B and the opposing end has an outlet 610.

The actuation rod 612 is disposed in the first compartment 607A and is moveable in the longitudinal direction of the outer housing 602. The actuation rod 612 comprises a peripheral wall with a space formed therein (not shown) that receives the biasing means. The nicotine delivery system 601 has first and second mating portions comprising male and female screw threads 615A, 615B respectively. The male screw thread 615A is formed on the outside of the peripheral wall of the actuation rod 612 and is configured to engage with the female screw thread 615B that is held in a fixed position on the inside of the first compartment 607A. The male and female screw threads 615A, 615B are configured so that the actuation rod 612 is urged in the longitudinal direction of the outer housing 602 when the actuation rod 612 is rotated relative therewith.

The biasing means 614 comprises a torsion spring that is configured to bias the actuation rod 612 to rotate in a direction so that the actuation rod 612 is urged towards the mouthpiece 605 due to interaction of the male and female screw threads 615A, 615B. Prior to first use of the nicotine delivery system 601, the torsion spring is pre-wound so that energy is stored in the spring that may later be utilized to bias the actuation rod 612. The pre-winding of the torsion spring 614 may be carried out during manufacture and assembly of the nicotine delivery system. Alternatively, it may be wound by a user prior to first use.

The actuation rod 612 is fixed to a friction wheel 616. The friction pad 613B is configured to be selectively engaged with the friction wheel 616 to prevent the friction wheel 616, and thus the actuation rod 612, from rotating relative to the outer housing 602. In one embodiment, the friction pad 613B and/or the surface of the friction wheel 614 may be textured to improve the friction therebetween.

The inside of the first compartment 607A is sealed from the inside of the canister 608 and the outlet channel 606A and the inside of the second compartment 607B is fluidly communicated with the end of the mouthpiece 605 by the suction channel 505B. Therefore, when the user sucks on the mouthpiece 605 to draw formulation through the outlet channel 606A, air in the second compartment 607B is sucked through the suction channel 606B and therefore the pressure in the second compartment 607B reduces so that it is less than the pressure in the first compartment 607A. This causes the diaphragm 613A to be urged away from the actuation rod 612 so that it deforms and the volume in the second chamber 607B decreases. The friction pad 613B comprises a rigid member that extends from the surface of the diaphragm and has a curved pad portion at an end thereof that is configured to engage with the friction wheel 616 to act as a brake to selectively prevent the actuation rod 612 from rotating relative to the outer housing 602.

When the nicotine delivery system is not in use, the friction pad 613B is urged against the friction wheel 616 and the friction therebetween holds the actuation rod 612 in a stationary position. When the user sucks on the mouthpiece 605 so that air is drawn out of the second compartment 607B and the diaphragm 613A is urged away from actuation rod 612, the friction pad 613B is urged away from the surface of the friction wheel 616 and the actuation rod 612 is free to rotate and therefore is urged towards the mouthpiece 605 due to interaction of the male and female screw threads 615A, 615B. When the user removes the nicotine delivery system 601 from their mouth, air flows back into the second compartment 607B, via the suction channel 606B. The diaphragm 613A is manufactured from a resilient material and is configured so that when the air flows back into the second compartment 607B the diaphragm 613A will move back towards the actuation rod 612 so that the friction pad 613B is urged back against the friction wheel 616 and the actuation rod 612 is prevented from rotating. Therefore, the actuation rod 612 is incrementally moveable in the outer housing 602 in the longitudinal direction thereof towards the mouthpiece 605.

As with the first embodiment, a pressure relief valve (not shown) is disposed between the outlet 610 and the outlet channel 606A and is configured to permit the flow of formulation from the chamber 608B to the outlet channel 606A when the pressure of the formulation in the chamber 608B reaches a pressure set-point. The actuation rod 612 abuts the piston 609 and so when the actuation rod 612 is moved incrementally upon actuation of the actuator 613 the piston 609 is slid within the chamber 608B towards the barrel outlet 610, causing the pressure of the formulation in the chamber 608B to increase above the pressure set-point required to open the pressure relief valve. Therefore, upon actuation of the actuator 613, formulation flows from the outlet 610, through the pressure relief valve, and out of the mouthpiece outlet channel 606A. The pressure in the chamber 608B then reduces to below the pressure set-point and the pressure relief valve closes. The actuator 613 may then again be actuated by the user to expel further doses of formulation from the mouthpiece 605 until the piston 609 has been slid relative to the chamber 608B to a position wherein it lies proximate to the outlet 610. As the actuation rod 612 urges the piston 609 relative to the chamber 608B by a predetermined distance upon each actuation of the actuator 613, a set amount dosage of formulation is released upon each actuation.

A damper 617 is connected to the actuation rod 612 and provides a moment of inertia to damp the motion provided by the torsion spring 614. In the above embodiment, the damper comprises a plurality of fins 617A to increase its moment of inertia to increase the amount of damping of the motion of the torsion spring 614. In an alternate embodiment, the moment of inertia of the damper may be increased by manufacturing it from a dense material, for example, lead or tungsten, to increase its mass. In yet another embodiment, the damper may be omitted.

Although in the above described embodiment the first and second mating portions comprise male and female screw threads 615A, 615B, in an alternate embodiment (not shown) one of the male and female screw threads 615A, 615B may be omitted and replaced with a protrusion that engages with the thread of the other of the male and female screw threads 615A, 615B to translate rotational movement of the piston rod 612 into movement of the piston rod 612 in the axial direction.

Although in the above described embodiment the actuator 613 comprises a diaphragm 613A that is actuated by the user, in an alternate embodiment the diaphragm 613A is omitted and replaced with an actuator of the type described in the previous embodiments. For example, the actuator may comprise a push button that is connected to the friction pad 613B and is configured to urge the friction pad 613B away from the friction wheel 616 upon actuation by the user so that the actuation rod 612 is free to rotate and urge the piston 609 relative to the barrel 608 to release formulation.

In the above described embodiments the nicotine delivery system comprises a pressure relief valve 11, 111, 211 that only permits formulation to be released when the formulation reaches a pressure set-point. Therefore, the pressure relief valve improves the spray quality of the nicotine delivery system by ensuring that the formulation is released at a pressure that is large enough for a spray is properly formed. However, in alternate embodiments (not shown), the pressure relief valve is omitted. In such embodiments, when the plunger is slid in the axial direction relative to the chamber in response to operation of the actuator by a user, a volume of formulation is displaced from the chamber and flows through the mouthpiece without the formulation in the chamber first having to reach a predetermined pressure set-point.

In some embodiments, such as any one of those discussed above, the formulation may contain nicotine. In some embodiments, such as any one of those discussed above, the formulation may comprise tobacco. For example, the formulation may be a non-tobacco-containing material or a tobacco-containing-material. The formulation may comprise one or more of tobacco, tobacco derivatives, tobacco extracts, or tobacco substitutes. The formulation may also include other, non-tobacco, products, which, depending on the product, may or may not contain nicotine.

In some embodiments, such as any one of those discussed above, the formulation may comprise one or more flavors or flavorants. As used herein, the terms "flavor" and "flavorant" refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder.

In some embodiments, such as any one of those discussed above, the formulation may be in an aqueous form or may be in a non-aqueous form, such as a powder form or a non-aqueous liquid form.

Although the above described specific combinations of features, it should be recognized as being within the scope of that which is claimed that features of different embodiments may be combined. For example, embodiments having a diaphragm may instead comprise a push button.

In order to address various issues and advance the art, the entirety of this disclosure shows by way of illustration various embodiments in which that which is claimed may be practiced and provide for a superior nicotine delivery system. The advantages and features of the disclosure are of a representative sample of embodiments only, and are not exhaustive and/or exclusive. They are presented only to assist in understanding and teach the claimed features. It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

The invention claimed is:

1. A nicotine delivery system comprising:
a housing that has a longitudinal axis and which defines a chamber that is configured to receive a plunger and has an outlet for the passage of a formulation out of the chamber;
an actuating mechanism comprising an actuator and an actuation member, wherein the actuator cooperates with the actuation member such that when the plunger is received in the chamber the plunger and the chamber slide relative to each other, parallel to the longitudinal axis, by a predetermined incremental distance in response to each operation of the actuator by a user to displace a predetermined volume of formulation from the chamber through said outlet;
a first biasing means that is configured to urge the actuation member in a first axial direction that is parallel to the longitudinal axis; and
a protrusion and a first track, the first track having a plurality of stopper surfaces,
wherein, in response to each operation of the actuator by a user, the protrusion is brought out of engagement with a corresponding one of the plurality of stopper surfaces, with the first biasing means consequently causing displacement of the protrusion relative to the first track in the first axial direction, bringing the protrusion into engagement with a consecutive one of the plurality of stopper surfaces, which holds the protrusion against urging by the first biasing means in the first axial direction, until a subsequent operation of the actuator by a user.

2. A nicotine delivery system according to claim 1, wherein the actuator is moveable in a direction transverse to the longitudinal axis to cause the plunger and the chamber to slide relative to each other.

3. A nicotine delivery system according to claim 2, wherein the actuator is mounted to the housing and comprises a button that is depressible inwardly towards the axis to displace the actuation member;
 wherein the actuator is slidably received in an aperture in the housing, or wherein the actuator is pivotally mounted to the housing.

4. A nicotine delivery system according to claim 1, wherein one of the actuator and actuation member comprises the protrusion and the other of the actuator and actuation member comprises the first track and wherein the actuator is moveable relative to the actuation member to displace the first track relative to the protrusion.

5. A nicotine delivery system according to claim 1, wherein the actuation member comprises one of the protrusion and first track and the other of the protrusion and first track is held in a fixed position relative to the housing, and wherein the actuator is configured to rotate the actuation member relative to the protrusion to urge the protrusion away from the corresponding one of the plurality of stopper surfaces;
 wherein the first track comprises a plurality of guide channels that each extends in the first axial direction and are arranged in a stepped formation; and
 wherein one of each of the plurality of stopper surfaces is disposed at a first end of each of the plurality of guide channels.

6. A nicotine delivery system according to claim 1, wherein the actuator is configured such that force exerted on the actuator upon actuation by the user is translated into a force that urges the actuation member in the first axial direction.

7. A nicotine delivery system according to claim 6, wherein one of the actuator and actuation member comprises a protrusion and the other of the actuator and actuation member comprises a track that is configured to translate displacement of the actuator in a direction transverse the longitudinal axis into displacement of the actuation member in the first axial direction;
 wherein the track comprises a guide channel that is angled with respect to the first axial direction and is configured to receive the protrusion; and
 wherein the guide channel is formed between first and second guide members, a flexible member and a receiving member of the track.

8. A nicotine delivery system according to claim 7, wherein the flexible member comprises a sloping portion that protrudes from a surface of the track and has a guide surface at an end thereof that is angled with respect to the first axial direction and is configured so that when the actuator is urged towards the actuation member in response to actuation by the user the protrusion is urged against the angled guide surface and is displaced relative to the track at an angle to the first axial direction;
 wherein the protrusion is urged against the sloped portion of the flexible member when the actuator is urged away from the actuation member so that the flexible member flexes to facilitate movement of the protrusion relative to the track in a direction transverse the longitudinal axis.

9. A nicotine delivery system according to claim 1, wherein the chamber is integrally formed with the housing, or wherein the chamber comprises a canister that is removably received in the housing; wherein the canister comprises the plunger.

10. A nicotine delivery system according to claim 1, comprising a mouthpiece with an outlet channel fluidly communicated with the chamber of the housing to expel formulation therefrom;
 wherein the nicotine delivery system comprises a pressure relief valve that opens to fluidly communicate the housing chamber with the outlet channel when the pressure in the chamber reaches a pressure set-point, the nicotine delivery system being configured so that the pressure set-point is reached when the plunger is slid relative to the chamber upon actuation of the actuator by the user.

11. A nicotine delivery system according to claim 1, comprising the formulation in the chamber, wherein the formulation contains nicotine.

12. A nicotine delivery system according to claim 11, wherein the formulation comprises tobacco.

13. A nicotine delivery system comprising:
 a housing that has a longitudinal axis and which defines a chamber that is configured to receive a plunger and has an outlet for the passage of a formulation out of the chamber;
 an actuation member that is configured such that when a plunger is received in the chamber the actuation member slides the plunger in a first axial direction that is parallel to the longitudinal axis into the chamber to displace formulation from the outlet in response to rotation of the actuation member relative to the housing;
 a first biasing means configured to urge the actuation member in a first rotational direction; and
 an actuator to hold the actuation member against urging by the first biasing means until actuation of the actuator by a user, whereupon the first biasing means causes the actuation member to rotate in the first rotational direction.

\* \* \* \* \*